(12) United States Patent
Quibell et al.

(10) Patent No.: US 7,846,935 B2
(45) Date of Patent: *Dec. 7, 2010

(54) FURO[3,2-B]PYRROL-3-ONE DERIVATIVES AND THEIR USE AS CYSTEINYL PROTEINASE INHIBITORS

(75) Inventors: Martin Quibell, Cambridge (GB); John Paul Watts, Cambridge (GB)

(73) Assignee: Amura Therapeutics Limited, Madingley (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/319,556

(22) Filed: Jan. 8, 2009

(65) Prior Publication Data

US 2009/0203714 A1 Aug. 13, 2009

Related U.S. Application Data

(63) Continuation of application No. PCT/GB2007/002630, filed on Jul. 13, 2007.

(30) Foreign Application Priority Data

Jul. 14, 2006 (GB) ................... 0614046.1

(51) Int. Cl.
 *A61K 31/496* (2006.01)
 *A61K 31/454* (2006.01)
 *C07D 491/08* (2006.01)
 *C12Q 1/37* (2006.01)

(52) U.S. Cl. .................. 514/254.08; 514/321; 544/373; 546/198; 435/23

(58) Field of Classification Search ........................ None
See application file for complete search history.

(56) References Cited

FOREIGN PATENT DOCUMENTS

| WO | WO-02/057270 A1 | 7/2002 |
|---|---|---|
| WO | 2005/066180 | * 7/2005 |

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Martin Quibell, et al.; "Bicyclic peptidomimetic tetrahydrofuro[3,2-*b*]pyrrol-3-one and hexahydrofuro[3,2-*b*]pyridine-3-one based scaffolds: synthesis and cysteinyl proteinase inhibition"; Bioorganic & Medicinal Chemistry; 12; (2004; pp. 5689-5710.
Martin Quibel, et al.; "Synthesis and evaluation of cis-hexahydropyrrolo[3-2-*b*]pyrrol-3-one peptidomimetic inhibitors of CAC1 cysteinyl proteinases"; Bioorganic & Medicinal Chemistry; 12; (2005); pp. 609-625.

* cited by examiner

*Primary Examiner*—Emily Bernhardt
(74) *Attorney, Agent, or Firm*—Edwards Angell Palmer & Dodge LLP; Kathleen Williams; Weiying Yang

(57) ABSTRACT

The present invention relates to compounds of formula (I), and pharmaceutically acceptable salts thereof,

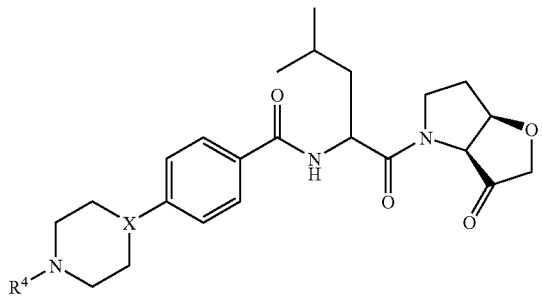

(I)

wherein:
X is CH or N; and
$R^4$ is optionally substituted $C_{3-8}$ alkyl or optionally substituted $C_{3-8}$ cycloalkyl.

The invention further relates to pharmaceutical compositions comprising compounds of formula (I), and the use of such compounds in the treatment of a disease selected from osteoporosis, Paget's disease, Chagas's disease, malaria, gingival diseases, hypercalaemia, metabolic bone disease, diseases involving matrix or cartilage degradation, and bone cancer disorders such as bone metastases and associated pain.

12 Claims, No Drawings

FURO[3,2-B]PYRROL-3-ONE DERIVATIVES AND THEIR USE AS CYSTEINYL PROTEINASE INHIBITORS

CROSS-REFERENCE TO RELATED APPLICATIONS

This application is a continuation of PCT application no. PCT/GB2007/002630, filed on Jul. 13, 2007, which claims priority to GB Patent Application No. 0614046.1, filed Jul. 14, 2006 The contents of these applications are incorporated herein by reference in their entirety.

The present invention relates to compounds that are inhibitors of cysteine proteinases, pharmaceutical compositions containing said compounds, and their use in therapy. More specifically, but not exclusively, the invention relates to compounds that are inhibitors of cathepsin K and related cysteine proteinases of the CA clan. Such compounds are particularly useful for the in vivo therapeutic treatment of diseases in which participation of a cysteine proteinase is implicated.

BACKGROUND TO THE INVENTION

Proteinases form a substantial group of biological molecules which to date constitute approximately 2% of all the gene products identified following analysis of several completed genome sequencing programmes. Proteinases have evolved to participate in an enormous range of biological processes, mediating their effect by cleavage of peptide amide bonds within the myriad of proteins found in nature. This hydrolytic action is performed by initially recognising, then binding to, particular three-dimensional electronic surfaces displayed by a protein, which align the bond for cleavage precisely within the proteinase catalytic site. Catalytic hydrolysis then commences through nucleophilic attack of the amide bond to be cleaved either via an amino acid side-chain of the proteinase itself, or through the action of a water molecule that is bound to and activated by the proteinase. Proteinases in which the attacking nucleophile is the thiol side-chain of a Cys residue are known as cysteine proteinases. The general classification of 'cysteine proteinase' contains many members found in a wide range of organisms from viruses, bacteria, protozoa, plants and fungi to mammals.

Cathepsin K and indeed many other crucial proteinases belong to the papain-like CAC1 family. Cysteine proteinases are classified into 'clans' based upon a similarity in the three-dimensional structure or a conserved arrangement of catalytic residues within the proteinase primary sequence. Additionally, 'clans' may be further classified into 'families' in which each proteinase shares a statistically significant relationship with other members when comparing the portions of amino acid sequence which constitute the parts responsible for the proteinase activity (see Barrett, A. J et a, in 'Handbook of Proteolytic Enzymes', Eds. Barrett, A. J., Rawlings, N. D., and Woessner, J. F. Publ. Academic Press, 1998, for a thorough discussion).

To date, cysteine proteinases have been classified into five clans, CA, CB, CC, CD and CE (Barrett, A. J. et a, 1998). A proteinase from the tropical papaya fruit 'papain' forms the foundation of clan CA, which currently contains over 80 distinct and complete entries in various sequence databases, with many more expected from the current genome sequencing efforts. Proteinases of clan CA/family C1 have been implicated in a multitude of house-keeping roles and disease processes. e.g. human proteinases such as cathepsin K (osteoporosis, osteoarthritis), cathepsin S (multiple sclerosis, rheumatoid arthritis, autoimmune disorders), cathepsin L (metastases), cathepsin B (metastases, arthritis), cathepsin F (antigen processing), cathepsin V (T-cell selection), dipeptidyl peptidase I (granulocyte serine proteinase activation) or parasitic proteinases such as falcipain (malaria parasite *Plasmodium falciparum*) and cruzipain (*Trypanosoma cruzi* infection). Recently a bacterial proteinase, staphylopain (*S. aureus* infection) has also been tentatively assigned to clan CA.

X-ray crystallographic structures are available for a range of the above mentioned proteinases in complex with a range of inhibitors e.g. papain (PDB entries, 1pad, 1pe6, 1pip, 1pop, 4pad, 5pad, 6pad, 1ppp, 1the, 1csb, 1huc), cathepsin K (1au0, 1au2, 1au3, 1au4, 1atk, 1mem, 1bgo, 1ayw, 1ayu, 1 nl6, 1nlj, 1q6k, 1snk, 1tu6), cathepsin L (1cs8, 1mhw), cathepsin S (1glo, 1ms6, 1npz), cathepsin V (1fh0), dipeptidyl peptidase I (1jqp, 1k3b), cathepsin B (1gmy, 1csb), cathepsin F (1m6d), cruzain (a recombinant form of cruzipain see Eakin, A. E. et al, 268(9), 6115-6118, 1993) (1ewp, 1aim, 2aim, 1F29, 1F2A, 1F2B, 1F2C), staphylopain (1cv8). Each of the structures displays a similar overall active-site topology, as would be expected by their 'clan' and 'family' classification and such structural similarity exemplifies one aspect of the difficulties involved in discovering a selective inhibitor of cathepsin K suitable for human use. However, subtle differences in terms of the depth and intricate shape of the active site groove of each CAC1 proteinase are evident, which may be exploited for selective inhibitor design. Additionally, many of the current substrate-based inhibitor complexes of CAC1 family proteinases show a series of conserved hydrogen bonds between the inhibitor and the proteinase backbone, which contribute significantly to inhibitor potency. Primarily a bidentate hydrogen-bond is observed between the proteinase Gly66 (C═O)/inhibitor N—H and the proteinase Gly66 (NH)/inhibitor (C═O), where the inhibitor (C═O) and (NH) are provided by an amino acid residue <u>NHCHRCO</u> that constitutes the S2 sub-site binding element within the inhibitor (see Berger, A. and Schecter, I. *Philos. Trans. R. Soc. Lond. [Biol.]*, 257, 249-264, 1970 for a description of proteinase binding site nomenclature). A further hydrogen-bond between the proteinase main-chain (C═O) of asparagine or aspartic acid (158 to 163, residue number varies between proteinases) and an inhibitor (N—H) is often observed, where the inhibitor (N—H) is provided by the S1 sub-site binding element within the inhibitor. Thus, the motif X—<u>NHCHR CO</u>—<u>NH</u>—Y is widely observed amongst the prior art substrate-based inhibitors of CAC1 proteinases.

Cathepsin K is thought to be significant in diseases involving excessive loss of bone or cartilage. Bone consists of a protein matrix incorporating hydroxyapatite crystals. About 90% of the structural protein of the matrix is type I collagen, with the remainder comprising various non-collagenous proteins such as osteocalcin, proteoglycans, osteopontin, osteonectin, thrombospondin, fibronectin and bone sialoprotein.

Skeletal bone is not a static structure but continually undergoes a cycle of bone resorption and replacement. Bone resorption is carried out by osteoclasts, which are multinuclear cells of haematopoietic lineage. Osteoclasts adhere to the bone surface and form a tight sealing zone. The membrane on the apical surface of the osteoclasts is folded so as to create a closed extracellular compartment between the osteoclast and the bone surface, which is acidified by proton pumps in the osteoclast membrane. Proteolytic enzymes are secreted into the compartment from the osteoclast. The high acidity in the compartment causes the hydroxyapatite at the surface of the bone to be dissolved and the proteolytic enzymes break down the protein matrix causing a resorption lacuna to be formed. Following bone resorption, osteoblasts produce a new protein matrix that is subsequently mineralised.

In disease states such as osteoporosis and Paget's disease, the bone resorption and replacement cycle is disrupted leading to a net loss of bone with each cycle. This leads to weakening of the bone and therefore to increased risk of bone fracture.

Cathepsin K is expressed at a high level in osteoclasts and is therefore thought to be essential for bone resorption. Thus, selective inhibition of cathepsin K is likely to be effective in the treatment of diseases involving excessive bone loss. These include osteoporosis, gingival diseases such as gingivitis and periodontitis, Paget's disease, hypercalaemia of malignancy and metabolic bone disease.

In addition to osteoclasts, high levels of cathepsin K are also found in chondroclasts from the synovium of osteoarthritic patients. It therefore appears that cathepsin K inhibitors will be of use in the treatment of diseases involving matrix or cartilage degradation, in particular osteoarthritis and rheumatoid arthritis.

Elevated levels of cathepsin K are also found in metastatic neoplastic cells which suggests that cathepsin K inhibitors may also be useful for treating certain neoplastic diseases.

In the prior art, the development of cysteine proteinase inhibitors for human use has recently been an area of intense activity (e.g. see Deaton, D. N. and Kumar, S., Prog. Med. Chem. 42, 245-375, 2004; Bromme, D. and Kaleta, J., Curr. Pharm. Des., 8, 1639-1658, 2002; Kim, W. and Kang, K., Expert Opin. Ther. Patents, 12(3), 419-432, 2002; Leung-Toung, R. et al. Curr. Med. Chem., 9, 979-1002, 2002; Lecaille, F. et al., Chem. Rev., 102, 4459-4488, 2002; Hernandez, A. A. and Roush, W. R., Curr. Opin. Chem. Biol., 6, 459-465, 2002). Considering the CAC1 family members, particular emphasis has been placed upon the development of inhibitors of human cathepsins, primarily cathepsin K (osteoporosis), cathepsin S (autoimmune disorders), cathepsin L (metastases), cathepsin B (metastases, arthritis), cathepsin F (antigen processing), cathepsin V (T-cell selection) and dipeptidyl peptidase I (granulocyte serine proteinase activation), through the use of peptide and peptidomimetic nitriles (e.g. see WO-A-03041649, WO-A-03037892, WO-A-03029200, WO-A-02051983, WO-A-02020485, US-A-20020086996, WO-A-01096285, WO-A-0109910, WO-A-0051998, WO-A-0119816, WO-A-9924460, WO-A-0049008, WO-A-0048992, WO-A-0049007, WO-A-0130772, WO-A-0055125, WO-A-0055126, WO-A-0119808, WO-A-0149288, WO-A-0147886), linear and cyclic peptide and peptidomimetic ketones (e.g. see Veber, D. F. and Thompson, S. K., Curr. Opin. Drug Discovery Dev., 3(4), 362-369, 2000, WO-A-02092563, WO-A-02017924, WO-A-01095911, WO-A-0170232, WO-A-0178734, WO-A-0009653, WO-A-0069855, WO-A-0029408, WO-A-0134153 to WO-A-0134160, WO-A-0029408, WO-A-9964399, WO-A-9805336, WO-A-9850533), ketoheterocycles (e.g. see WO-A-02080920, WO-A-03042197, WO-A-WO-A-03024924, WO-A-0055144, WO-A-0055124), monobactams (e.g. see WO-A-0059881, WO-A-9948911, WO-A-0109169), α-ketoamides (e.g. see WO-A-03013518), cyanoamides (WO-A-01077073, WO-A-01068645), dihydro pyrimidines (e.g. see WO-A-02032879) and cyanoaminopyrimidines (e.g. see WO-A-03020278, WO-A-03020721).

The prior art describes potent in vitro inhibitors, but also highlights the many difficulties in developing a human therapeutic. For example, WO-A-9850533 and WO-A-0029408 describe compounds that may be referred to as cyclic ketones (e.g. 1'a-f) and are inhibitors of cysteine proteinases with a particular reference towards papain family proteinases and as a most preferred embodiment, cathepsin K. WO-A-9850533 describes compounds subsequently detailed in the literature as potent inhibitors of cathepsin K with good oral bioavailability (Witherington, J., 'Tetrahydrofurans as Selective Cathepsin K Inhibitors', RSC meeting, Burlington House, London, 1999). The compounds of WO-A-9850533 were reported to bind to cathepsin K through the formation of a reversible covalent bond between the tetrahydrofuran carbonyl and the active site catalytic cysteine residue (Witherington, J., 1999). Additionally, the same cyclic ketone compounds are described in WO-A-9953039 as part of a wide-ranging description of inhibitors of cysteine proteinases associated with parasitic diseases, with particular reference to the treatment of malaria by inhibition of falcipain.

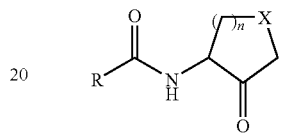

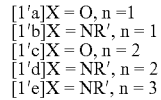

[1'a] X = O, n = 1
[1'b] X = NR', n = 1
[1'c] X = O, n = 2
[1'd] X = NR', n = 2
[1'e] X = NR', n = 3

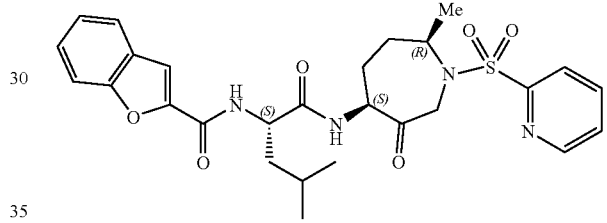

[1'f] SB-462795, relacatib

Prior Art Cyclic Inhibitors of Cathepsin K

The initial cyclic inhibitors of GSK were based upon potent, selective and reversible 3-amido-tetrahydrofuran-4-ones [1'a], 3-amidopyrrolidin-4-ones [1'b], 4-amido-tetrahydropyran-3-ones [1'c], 4-amidopiperidin-3-ones [1'd] and 4-amidoazepan-3-ones [1'e, 1'f] (shown above) [see (a) Marquis, R. W. et al, J. Med. Chem. 2001, 44, 725, and references cited therein; (b) Marquis, R. W. et al, J. Med. Chem. 2001, 44, 1380, and references cited therein; (c) Yamashita, D. S. et al, J. Med. Chem. 2006, 49(5), 1597-1612].

Further studies revealed that cyclic ketones [1'], in particular the five-membered ring analogues [1'a] and [1'b], suffered from configurational instability due to facile epimerisation at the centre situated α to the ketone [Marquis, R. W. et al, J. Med. Chem. 2001, 44, 1380; Fenwick, A. E. et al., J. Bioorg. Med. Chem. Lett. 2001, 11, 199; WO 00/69855]. This precluded the pre-clinical optimisation of inhibitors of formulae [1'a-d] and led to the development of the configurationally more stable azepanone series [1'e], providing the cathepsin K inhibitor clinical candidate relacatib [1'f]. However, literature clearly states that azepanones are still prone to epimerisation and indeed relacatib [1'f] is reported to exist as a 9:1 thermodynamic mixture of 4-S and 4-R isomers [Yamashita, D. S. et al, J. Med. Chem., 2006, 49(5), 1597-1612]. As an alternative to the ring expansion approach, alkylation of the α-carbon removes the ability of cyclic ketones [1'] to undergo α-enolisation and hence leads to configurational stability. However, studies have shown that α-methylation in the 3-amidopyrrolidin-4-one [1'b] system results in a substantial loss in potency versus cathepsin K from $K_{i,app}$≈0.18 to 50 nM.

The cyclic ketone compounds of WO-A-0069855 are considered to be an advance on compounds of WO-A-9850533 due to the presence of the β-substituent on the cyclic ketone ring system that provides improved chiral stability to the α-carbon of the cyclic ketone ring system. However, the compounds of WO-A-0069855 and indeed those of WO-A-9850533 describe a requirement for the presence of the potential hydrogen-bonding motif X—NHCHRCO—NH—Y that is widely observed amongst the prior art substrate-based inhibitors of CAC1 proteinases.

More recent studies have investigated 5,5-bicyclic systems as inhibitors of CAC1 proteinases, for example, N-(3-oxo-hexahydrocyclopenta[b]furan-3a-yl)acylamide bicyclic ketones [2'] [(a) Quibell, M.; Ramjee, M. K., WO 02/57246; (b) Watts, J. et al, Bioorg. Med. Chem. 2004, 12, 2903-2925], tetrahydrofuro[3,2-b]pyrrol-3-one based scaffolds [3'] [(a) Quibell, M. WO02/57270; (b) Quibell, M. et al, Bioorg. Med. Chem., 2004, 12, 5689-5710], cis-6-oxohexahydro-2-oxa-1,4-diazapentalene and cis-6-oxo-hexahydropyrrolo[3,2-c]pyrazole based scaffolds [4'] [Wang, Y. et al, Bioorg. Med. Chem. Lett., 2005, 15, 1327-1331], and cis-hexahydropyrrolo[3,2-b]pyrrol-3-one based scaffolds [5'] [a) Quibell, M. WO04/07501; (b) Quibell, M. et al, Bioorg. Med. Chem., 2005, 13, 609-625].

[2']

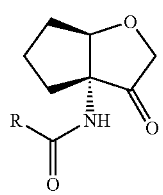

[3']

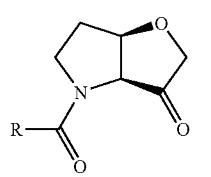

[4']

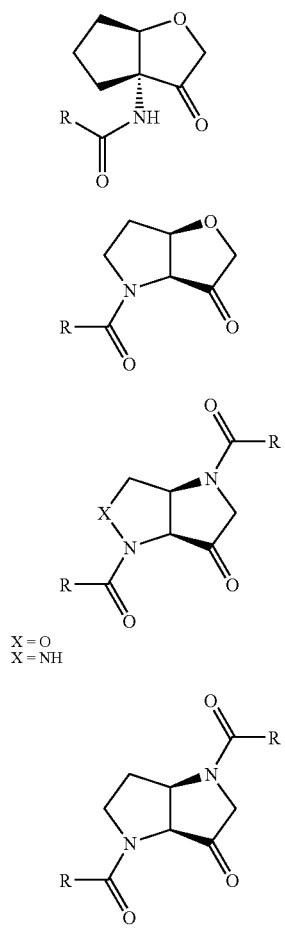

X = O
X = NH

[5']

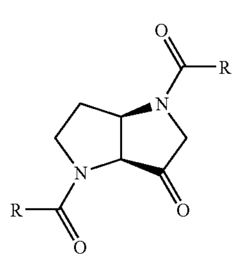

5,5-bicyclic Inhibitors of CAC1 Cysteinyl Proteinases

Studies have shown that the above-described 5,5-bicyclic systems exhibit promising potency as inhibitors of a range of therapeutically attractive mammalian and parasitic CAC1 cysteinyl proteinase targets. Moreover, the 5,5-bicyclic series are chirally stable due to a marked energetic preference for a cis-fused rather than a trans-fused geometry. This chiral stability provides a major advance when compared to monocyclic systems that often show limited potential for preclinical development due to chiral instability.

PCT applications WO-A-02057270 and WO-A-04007501 describe bicyclic compounds in which the chirality of the α-aminoketone is stabilised (for a review of energetic considerations within fused ring systems see (a) Toromanoff, E. *Tetrahedron Report No* 96, 36, 2809-2931, 1980; (b) Eliel, E. L. et. al. *Stereochemistry of Organic Compounds*, Wiley: New York, 1-1267, 1994). These compounds do not contain the X—NHCHRCO—NH—Y motif and yet the compounds are highly potent inhibitors across a broad range of CAC1 cysteine proteinases. In particular, certain of the compounds are potent and selective inhibitors of a range of mammalian and parasitic CAC1 proteinases.

More recently, Quibell, M. et al (*Bioorg. Med. Chem.* 12, 5689-5710, 2004) disclosed two potent and selective cathepsin K inhibitors having a tetrahydrofuro[3,2-b]pyrrol-3-one core, along with in vitro potency and in vitro selectivity data. Further kinetic parameters such as enzyme association (kon) and dissociation (koff) rates were disclosed, as well as basic physiochemical parameters such as plasma and microsome stability, Caco-2 permeability and LogD ($pH_{7.4}$) measurements.

The present inventors have now discovered a small genus of tetrahydrofuro[3,2-b]pyrrol-3-ones that exhibit potent in vitro inhibition versus human cathepsin K. Advantageously, the claimed compounds also display favourable pharmacokinetic properties and potent osteoclast activity versus human cells and a highly preferred subset exhibit potent inhibitory activity in rat osteoclasts.

STATEMENT OF INVENTION

A first aspect of the invention relates to compounds of general formula (I), and pharmaceutically acceptable salts, hydrates, solvates, complexes and prodrugs thereof, (I)

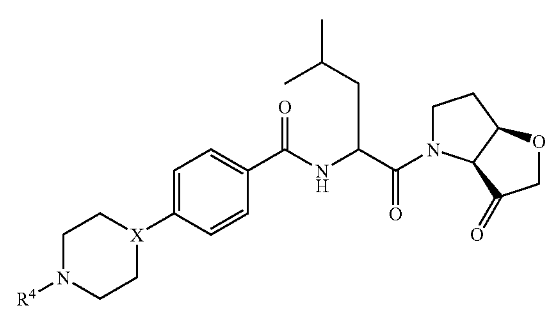

wherein:

X is CH or N; and $R^4$ is optionally substituted $C_{3-8}$ alkyl or optionally substituted $C_{3-8}$ cycloalkyl.

As mentioned above, compounds of formula (I) exhibit surprisingly high efficacies for human cathepsin K. Indeed, all of the compounds prepared to date exhibit potent in vitro inhibition versus human cathepsin K with Ki<50 nM. Furthermore, preferred compounds of formula (I) also exhibit desirable pharmacokinetic properties and potent cross species osteoclast activity, contrary to many cathepsin K inhibitors known in the art. In addition, preferred compounds of formula (I) also exhibit surprisingly good stability in plasma and microsome assays.

A second aspect of the invention relates to a pharmaceutical or veterinary composition comprising a compound of formula (I) and a pharmaceutically acceptable or veterinarily acceptable diluent, excipient and/or carrier.

A third aspect of the invention relates to a process for preparing a pharmaceutical or veterinary composition as defined above, said process comprising admixing a compound of the invention with a pharmaceutically acceptable or veterinarily acceptable diluent, excipient and/or carrier.

A fourth aspect of the invention relates to compounds of formula (I) for use in medicine.

A fifth aspect of the invention relates to the use of a compound of formula (I) in the preparation of a medicament for treating a disease selected from osteoporosis, Paget's disease, Chagas's disease, malaria, gingival diseases, hypercalaemia, metabolic bone disease, diseases involving matrix or cartilage degradation, bone cancer disorders such as bone metastases and associated pain.

A sixth aspect of the invention relates to a method of inhibiting a cysteine proteinase in a cell, said method comprising contacting said cell with a compound of formula (I).

A seventh aspect of the invention relates to method of inhibiting a cysteine proteinase in a subject, said method comprising administering to the subject a pharmacologically effective amount of a compound of formula (I).

An eighth aspect of the invention relates to a method of treating a disease selected from osteoporosis, Paget's disease, Chagas's disease, malaria, gingival diseases, hypercalaemia, metabolic bone disease, diseases involving matrix or cartilage degradation, bone cancer disorders such as bone metastases and associated pain, in a subject, said method comprising administering to the subject a pharmacologically effective amount of a compound of formula (I).

A ninth aspect of the invention relates to the use of a compound according to the invention in an assay for identifying further candidate compounds capable of inhibiting one or more cysteine proteinases.

A tenth aspect of the invention relates to the use of a compound of formula (I) in the validation of a known or putative cysteine proteinase as a therapeutic target.

An eleventh aspect of the invention relates to a process of preparing a compound of formula (I).

DETAILED DESCRIPTION

The term 'alkyl' as applied herein includes stable straight and branched chain aliphatic carbon chains which may be optionally substituted. Preferred examples include methyl, ethyl, n-propyl, isopropyl, n-butyl, isobutyl, t-butyl, pentyl, isopentyl, hexyl, heptyl and any simple isomers thereof. Suitable substituents include, for example, one or more $C_{1-6}$ alkoxy, OH, COOH, COOMe, $NH_2$, $NMe_2$, NHMe, $NO_2$, CN, $CF_3$ and/or halo groups. Additionally, where the alkyl group contains two or more contiguous carbon atoms, an alkene group (—CH=CH—) or alkyne group (—C≡C—) may be present. Furthermore, the alkyl group may optionally contain one or more heteroatoms for example, to give ethers, thioethers, sulphones, sulphonamides, substituted amines, amidines, guanidines, carboxylic acids, carboxamides. If the heteroatom is located at a chain terminus then it is appropriately substituted with one or two hydrogen atoms. For example, the group $CH_3$—$CH_2$—O—$CH_2$—$CH_2$— is defined within 'alkyl' as a $C_4$ alkyl that contains a centrally positioned heteroatom whereas the group $CH_3$—$CH_2$—$CH_2$—$CH_2$— is defined within 'alkyl' as an unsubstituted $C_4$ alkyl.

Preferably, the alkyl group is a $C_{3-8}$ alkyl group, more preferably a $C_{3-6}$ group, even more preferably a $C_{3-4}$ alkyl group.

As used herein, the term "cycloalkyl" refers to a cyclic alkyl group (i.e. a carbocyclic ring) which may be substituted (mono- or poly-) or unsubstituted. Suitable substituents include, for example, one or more $C_{1-6}$ alkyl, $C_{1-6}$ alkoxy, OH, COOH, COOMe, $NH_2$, $NMe_2$, NHMe, $NO_2$, CN, $CF_3$ and/or halo groups. Preferably, the cycloalkyl group is a $C_{3-8}$ cycloalkyl group, more preferably a $C_{3-6}$-cycloalkyl, even more preferably a $C_{3-4}$ cycloalkyl group. Examples include cyclopropyl, cyclobutyl, cyclopentyl, cyclohexyl and the like. In addition, the carbocyclic ring itself may optionally contain one or more heteroatoms, for example, to give a heterocycloalkyl group such as tetrahydrofuran, pyrrolidine, piperidine, piperazine or morpholine.

'Halogen' or 'halo' as applied herein encompasses F, Cl, Br, I.

'Heteroatom' as applied herein encompasses O, S, P and N, more preferably, O, S and N.

The present invention includes all salts, hydrates, solvates, complexes and prodrugs of the compounds of this invention. The term "compound" is intended to include all such salts, hydrates, solvates, complexes and prodrugs, unless the context requires otherwise.

In particular, the skilled person will appreciate that the ketone group of the bicycle core of compounds of formula (I) may exist in alternative forms such as the hydrate (as shown below), and the invention extends to all such alternative forms.

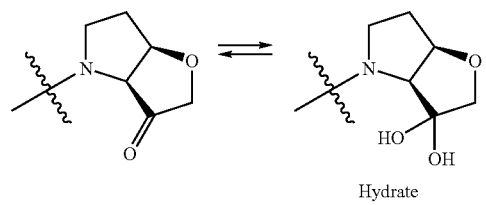

Hydrate

Abbreviations and symbols commonly used in the peptide and chemical arts are used herein to describe compounds of the present invention, following the general guidelines presented by the IUPAC-IUB Joint Commission on Biochemical Nomenclature as described in *Eur. J. Biochem.*, 158, 9-, 1984. Compounds of formula (I) and the intermediates and starting materials used in their preparation are named in accordance with the IUPAC rules of nomenclature in which the characteristic groups have decreasing priority for citation as the principle group.

In one preferred embodiment, the compound of the invention is of formula Ia

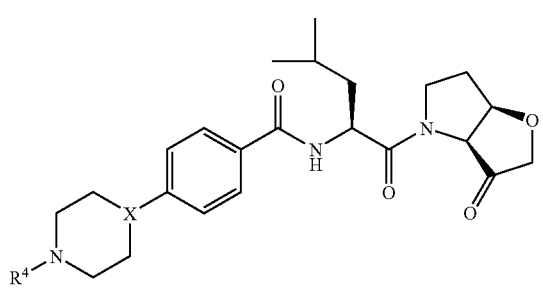

(Ia)

wherein X and R⁴ are as defined above.

Thus, in one preferred embodiment, the isopropylmethyl group is of the S-configuration such that the central moiety is the aminoacid (S)-leucine.

In one preferred embodiment, X is CH.
In another preferred embodiment, X is N.
In one preferred embodiment, R⁴ is an unsubstituted $C_{3-6}$ cycloalkyl group.
In one preferred embodiment, R⁴ is a $C_{3-6}$ alkyl group.
Yet more preferably, R⁴ is selected from n-propyl, isopropyl, cyclopropyl, n-butyl, s-butyl, i-butyl, tert-butyl, cyclobutyl and 2-methoxyethyl.

Even more preferably still, R⁴ is selected from n-propyl, isopropyl, cyclopropyl, cyclobutyl and 2-methoxyethyl.

In one highly preferred embodiment, the compound of the invention is selected from the following:
N—((S)-4-methyl-1-oxo-1-((3aS,6aR)-3-oxo-dihydro-2H-furo[3,2-b]pyrrol-4(5H,6H,6aH)-yl)pentan-2-yl)-4-(4-propylpiperazin-1-yl)benzamide;
N—((S)-4-methyl-1-oxo-1-((3aS,6aR)-3-oxo-dihydro-2H-furo[3,2-b]pyrrol-4(5H,6H,6aH)-yl)pentan-2-yl)-4-(1-propylpiperidin-4-yl)benzamide;
4-(4-isopropylpiperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(1-isopropylpiperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(4-(2-methoxyethyl)piperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(1-(2-methoxyethyl)piperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(4-cyclopropylpiperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(1-cyclopropylpiperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(4-cyclobutylpiperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;
4-(1-cyclobutylpiperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

In one highly preferred embodiment, the compound of the invention is selected from EXAMPLES 3, 4, 6 and 7 as described in the accompanying Examples section.

In another preferred embodiment, the compound of the invention is selected from EXAMPLES 3, 5 and 8 as described in the accompanying Examples.

In an even more preferred embodiment, the compound of the invention is EXAMPLE 3 as described in the accompanying Examples section.

Pharmaceutical Compositions

A further aspect of the invention relates to a pharmaceutical composition comprising a compound of the invention admixed with one or more pharmaceutically acceptable diluents, excipients or carriers. Other active materials may also be present, as may be considered appropriate or advisable for the disease or condition being treated or prevented.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and PJ Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

A prodrug may for example constitute a ketal or hemiketal derivative of the exocyclic ketone functionality present in the tetrahydro-furo[3,2-b]pyrrol-3-one scaffold.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Assays

Another aspect of the invention relates to the use of a compound of the invention as defined hereinabove in an assay for identifying further candidate compounds that influence the activity of one or cysteine proteinases.

Preferably, the assay is capable of identifying candidate compounds that are capable of inhibiting one or more CAC1 cysteine proteinases.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a cysteine proteinase in the presence of a known substrate of said enzyme and detecting any change in the interaction between said cysteine proteinase and said known substrate.

A further aspect of the invention provides a method of detecting the binding of a ligand to a cysteine proteinase, said method comprising the steps of:

(i) contacting a ligand with cysteine proteinase in the presence of a known substrate of said enzyme;

(ii) detecting any change in the interaction between said enzyme and said known substrate;

and wherein said ligand is a compound of the invention.

One aspect of the invention relates to a process comprising the steps of:

(a) performing an assay method described hereinabove;

(b) identifying one or more ligands capable of binding to a ligand binding domain; and (c) preparing a quantity of said one or more ligands.

Another aspect of the invention provides a process comprising the steps of:

(a) performing an assay method described hereinabove;

(b) identifying one or more ligands capable of binding to a ligand binding domain; and (c) preparing a pharmaceutical composition comprising said one or more ligands.

Another aspect of the invention provides a process comprising the steps of:

(a) performing an assay method described hereinabove;

(b) identifying one or more ligands capable of binding to a ligand binding domain;

(c) modifying said one or more ligands capable of binding to a ligand binding domain;

(d) performing the assay method described hereinabove;

(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders selected from osteoporosis, Paget's disease, Chagas's disease, malaria, gingival disease such as gingivitis or periodontitis, hypercalaemia, metabolic bone disease and diseases involving matrix or cartilage degradation, such as osteoarthritis, rheumatoid arthritis, neoplastic diseases and bone cancer disorders such as bone metastases and associated pain.

The above methods may be used to screen for a ligand useful as an inhibitor of one or more cysteine proteinases.

Compounds of general formula (I) are useful both as laboratory tools and as therapeutic agents. In the laboratory certain compounds of the invention are useful in establishing whether a known or newly discovered cysteine proteinase contributes a critical or at least significant biochemical function during the establishment or progression of a disease state, a process commonly referred to as 'target validation'.

According to a further aspect of the invention, there is provided a method of validating a known or putative cysteine proteinase as a therapeutic target, the method comprising:

(a) assessing the in vitro binding of a compound as described above to an isolated known or putative cysteine proteinase, providing a measure of potency; and optionally, one or more of the steps of:

(b) assessing the binding of the compound to closely related homologous proteinases of the target and general housekeeping proteinases (e.g. trypsin) to provide a measure of selectivity;

(c) monitoring a cell-based functional marker of a particular cysteine proteinase activity, in the presence of the compound; and (d) monitoring an animal model-based functional marker of a particular cysteine proteinase activity in the presence of the compound.

The invention therefore provides a method of validating a known or putative cysteine proteinase as a therapeutic target. Differing approaches and levels of complexity are appropriate to the effective inhibition and 'validation' of a particular target. In the first instance, the method comprises assessing the in vitro binding of a compound of general formula (I) to an isolated known or putative cysteine proteinase, providing a measure of 'potency'. An additional assessment of the binding of a compound of general formula (I) to closely related homologous proteinases of the target and general housekeeping proteinases (e.g. trypsin) provides a measure of 'selectivity'. A second level of complexity may be assessed by monitoring a cell-based functional marker of a particular cysteine proteinase activity, in the presence of a compound of general formula (I). For example, an 'osteoclast resorption assay' has been utilised as a cell-based secondary in vitro testing system for monitoring the activity of cathepsin K and the biochemical effect of proteinase inhibitors (e.g. see WO-A-9850533). An 'MHC-II processing—T-cell activation assay' has been utilised as a cell-based secondary in vitro testing system for monitoring the activity of cathepsin S and the biochemical effect of proteinase inhibitors (Shi, G-P., et al, *Immunity*, 10, 197-206, 1999). When investigating viral or bacterial infections such a marker could simply be a functional assessment of viral (e.g. count of mRNA copies) or bacterial loading and assessing the biochemical effect of proteinase inhibitors. A third level of complexity may be assessed by monitoring an animal model-based functional marker of a particular cysteine proteinase activity, in the presence of a compound of general formula (I). For example, murine models of *Leishmania* infection, *P. vinckei* infection, malaria (inhibition of falcipain) and *T. cruzi* infection (cruzipain), indicate that inhibition of cysteine proteinases that play a key role in pathogen propagation is effective in arresting disease symptoms, 'validating' said targets.

The invention therefore extends to the use of a compound of general formula (I) in the validation of a known or putative cysteine proteinase as a therapeutic target.

Biological Activity

Advantageously, the compounds of the present invention exhibit surprisingly high efficacies for human cathepsin K. Indeed, all of the compounds prepared to date exhibit potent in vitro inhibition versus human cathepsin K with Ki<50 nM (for example see table 1). In contrast, the majority of the eighty-two prior art compounds detailed in WO-A-02057270 were significantly less potent against human cathepsin K than the preferred compounds of the present invention (for example see table 2). Therefore preferred compounds of the present invention are 3-20 fold more potent in vitro against human cathepsin K than the most potent example from WO-A-02057270 and in the majority of examples greater than 1000-fold more potent.

Preferably, the compounds exhibit in vitro inhibition versus human cathepsin K with Ki<40 nM, more preferably <30 nM, even more preferably <20 nM, more preferably still <10 nM, and even more preferably <5 nM. The compounds of the invention exhibit high selectivity against other mammalian cathepsins displaying little or no inhibitory activity for cathepsins S, L, B and V at 1 µM compound.

The presently claimed compounds also exhibit desirable pharmacokinetic properties. Without wishing to be bound by theory, it is believed that the presence of a piperazine or piperidine ring moiety confers compounds of formula (I) with one or more of the following: favourable HLM stability, improved plasma stability and/or improved solubility, compared with other cathepsin K inhibitors known in the art (for example, those disclosed in WO 02/057270 and prior art compound 23/10 detailed in Quibell, M. et. al., Bioorg. Med. Chem. 13, 609-625, 2005; Quibell M, et al Bioorg. Med. Chem., 12, 5689-5710, 2004). In particular, results have shown that compounds of formula (I) as described herein exhibit surprisingly good stability in plasma and microsome assays. For example, preferred compounds of the present invention are significantly more stable in human plasma and against human liver microsomes, e.g. compare stability of prior art compound 23 with any of the presently preferred piperazine or piperidine ring moiety containing analogues (table 1).

In addition, presently claimed compounds exhibit potent osteoclast activity versus human and/or rat cells. A highly preferred sub-group of presently claimed compounds exhibit potent osteoclast activity verses human cells (e.g. compare human osteoclast data for EXAMPLES 3, 4, 6 and 7 (73-82% inhibition) with prior art EXAMPLE 1 (55% inhibition) and the closely related non-preferred EXAMPLE 2 (58% inhibition)).

In addition, a second highly preferred sub-group of presently claimed compounds, wherein $R^4$ is a straight alkyl chain exhibit potent osteoclast activity versus rat cells (e.g. compare rat osteoclast data for EXAMPLES 3, 5 and 8 with those where $R^4$ is a branched or cycloalkyl group [EXAMPLES 4, 6 and 7] detailed in table 1).

An even more highly preferred sub-group of presently claimed compounds, wherein $R^4$ is a straight alkyl chain and log D ($pH_{7.4}$) is greater than 1.0 exhibit potent osteoclast activity versus human and rat cells (e.g. compare human (73%) and rat (65%) osteoclast data for EXAMPLE 3 with those where $R^4$ is a straight alkyl chain and log D ($pH_{7.4}$) is less than 1.0 [e.g. EXAMPLE 5 human (57%), rat (65%); EXAMPLE 8 human (23%), rat (52%)] or where $R^4$ is a branched alkyl or cycloalkyl chain and log D ($pH_{7.4}$) is greater than 1.0 [e.g. EXAMPLE 4 human (74%), rat (25%); EXAMPLE 6 human (74%), rat (22%); EXAMPLE 7 human (82%), rat (40%);] detailed in table 1).

Data suggests that this cross species osteoclast activity is a feature common to the even more highly preferred sub-group of compounds of the present invention. The literature details significantly reduced potencies for many other cathepsin K inhibitor series when profiled against rat analogues (e.g. see Deaton, D. N. and Kumar, S. *Prog. In Med. Chem.* 42, 245-375, 2004), a factor that has caused major obstacles for the development of alternative series. Thus, even more highly preferred compounds may be distinguished further as those that show higher potency in human and rat osteoclast assays.

LogD is an experimentally determined characteristic of a compound that is considered to reflect the propensity of a compound to transfer across the lipid core of a membrane. LogD is defined as the logarithm of the distribution coefficient (D) at a selected pH, usually assumed to be measured in octanol/water. Without wishing to be bound by theory, it is believed that human osteoclast potency and experimentally determined Log D ($pH_{7.4}$) can be used as a means of further distinguishing highly preferred inhibitors of cathepsin K. For example, prior art compound EXAMPLE 1 which has the increased stability and high in vitro human cathepsin K potency that is afforded by the piperazine moiety, exhibits 55% inhibition of human osteoclast activity at 1 µM. EXAMPLE 2 that is a close analogue of prior art EXAMPLE 1 exhibits 58% inhibition of human osteoclast activity at 1 µM. In contrast, highly preferred compounds of the present invention which exhibit broadly similar high in vitro human cathepsin K potency when compared to EXAMPLES 1 and 2 show significantly increased inhibition of human osteoclast activity at 73-82% at 1 µM (see table 1, EXAMPLES 3, 4, 6, 7). Therefore highly preferred examples of the present invention show a surprising increase in human osteoclast potency when $LogD_{(7.4)}$ is greater than 1.0.

Therapeutic Use

Compounds of general formula (I) are useful for the in vivo treatment or prevention of diseases in which participation of a cysteine proteinase is implicated.

In particular, compounds of general formula I are inhibitors of a wide range of CAC1 cysteinyl proteinases for example cathepsin K, cathepsin S, cathepsin L, cathepsin F, cathepsin B, cathepsin V, cruzipains, falcipains and *leismania mexicana* CPB proteinase.

Preferably, the compound of general formula I is selective for cathepsin K. As used herein, the term "selective for cathepsin K" means that the inhibitor is selective for cathepsin K over one or more other mammalian CAC1 cysteinyl proteinases for example cathepsin S, cathepsin L, cathepsin F, cathepsin B and cathepsin V. Preferably, the inhibitor exhibits a selectivity ratio for cathepsin K over other mammalian CAC1 cysteinyl proteinases of greater than 2-fold, more preferably greater than 5-fold, more preferably greater than 10-fold, even more preferably greater than 25-fold, more preferably still, greater than 50-fold or 100-fold.

According to a further aspect of the invention, there is provided a compound of general formula (I) for use in medicine, especially for preventing or treating diseases in which the disease pathology may be modified by inhibiting a cysteine proteinase.

According to a further aspect of the invention, there is provided the use of a compound of general formula (I) in the preparation of a medicament for preventing or treating diseases in which the disease pathology may be modified by inhibiting a cysteine proteinase.

Certain cysteine proteinases function in the normal physiological process of protein degradation in animals, including humans, e.g. in the degradation of connective tissue. However, elevated levels of these enzymes in the body can result in pathological conditions leading to disease. Thus, cysteine proteinases have been implicated in various disease states, including but not limited to, infections by *Pneumocystis carinii, Trypsanoma cruzi, Trypsanoma brucei brucei* and *Crithidia fusiculata*; as well as in osteoporosis, osteoarthritis, rheumatoid arthritis, multiple sclerosis, chronic pain, autoimmunity, schistosomiasis, malaria, tumour metastasis, metachromatic leukodystrophy, muscular dystrophy, amytrophy, and the like (see WO-A-9404172 and EP-A-0603873 and references cited therein). Additionally, a secreted bacterial cysteine proteinase from *S. Aureus* called staphylopain has been implicated as a bacterial virulence factor (Potempa, J., et al. J. Biol. Chem., 262(6), 2664-2667, 1998).

The invention is useful in the prevention and/or treatment of each of the disease states mentioned or implied above. The present invention also is useful in a methods of treatment or prevention of diseases caused by pathological levels of cysteine proteinases, particularly cysteine proteinases of the papain superfamily, which methods comprise administering to an animal, particularly a mammal, most particularly a human, in need thereof a compound of the present invention. The present invention particularly provides methods for treating diseases in which cysteine proteinases are implicated, including infections by *Pneumocystis carinii, Trypsanoma cruzi, Trypsanoma brucei, Leishmania mexicana, Clostridium histolyticum, Staphylococcus aureus*, foot-and-mouth disease virus and *Crithidia fusiculta*; as well as in osteoporosis, osteoarthritis, rheumatoid arthritis, multiple sclerosis, chronic pain, autoimmunity, schistosomiasis, malaria, tumour metastasis, metachromatic leukodystrophy, muscular dystrophy, amytrophy.

Inhibitors of cathepsin K, particularly cathepsin K-specific compounds, are useful for the treatment of osteoporosis, Paget's disease, gingival diseases such as gingivitis and periodontitis, hypercalaemia of malignancy, metabolic bone disease, diseases involving matrix or cartilage degradation, in particular osteoarthritis and rheumatoid arthritis and neoplastic diseases.

Preferred features for each aspect of the invention are as for each other aspect mutatis mutandis.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica.

Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to inhibit the proteinase implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a cysteine proteinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiketals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

Synthesis

Synthesis of 5,5-Bicyclic Core

One aspect of the invention relates to a process of preparing a compound of formula (I) as defined above, said process comprising converting a compound of formula (II), where $R^5$ is a protecting group, into a compound of formula (I)

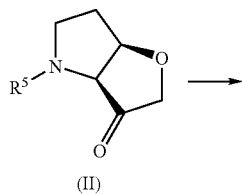

(II)

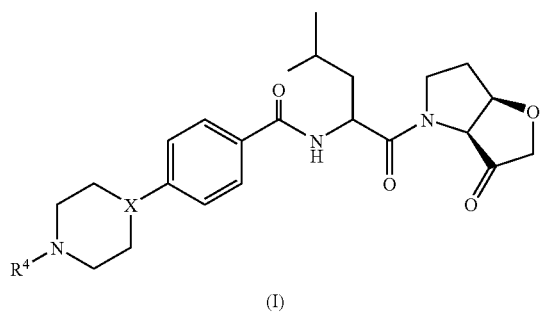

(I)

In one preferred embodiment, the process of the invention comprises the step of converting a compound of formula (III) into a compound of formula (II)

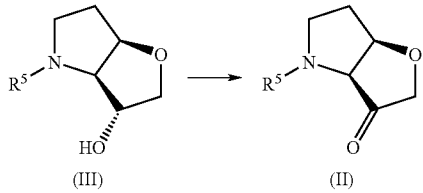

Any suitable oxidising agent may be used to convert the secondary alcohol group of (III) into the corresponding ketone (II). Suitable oxidising agents will be familiar to the skilled artisan. By way of example, the oxidation may be carried out via a Dess-Martin periodinane reaction [Dess, D. B. et al, J. Org. Chem. 1983, 48, 4155; Dess, D. B. et al, J. Am. Chem. Soc. 1991, 113, 7277], or via a Swern oxidation [Mancuso, A. J. et al, J. Org. Chem. 1978, 43, 2480]. Alternatively, the oxidation can be carried out using SO$_3$/pyridine/Et$_3$N/DMSO [Parith, J. R. et al, J. Am. Chem. Soc. 1967, 5505; U.S. Pat. No. 3,444,216, Parith, J. R. et al.], P$_2$O$_5$/DMSO or P$_2$O$_5$/Ac$_2$O [Christensen, S. M. et al., Organic Process Research and Development, 2004, 8, 777]. Other alternative oxidation reagents include activated dimethyl sulphoxide [Mancuso, A. J., Swern, D. J., Synthesis, 1981, 165], pyridinium chlorochromate [Pianeatelli, G. et al., Synthesis, 1982, 245] and Jones' reagent [Vogel, A, I., Textbook of Organic Chemistry, 6$^{th}$ Edition].

More preferably, the process comprises treating a compound of formula (III) with Dess-Martin periodinane. Preferably, the reaction is carried out using dichloromethane as solvent.

In a more preferred embodiment the process of the invention comprises the step of converting a compound of formula (IV) into a compound of formula (III)

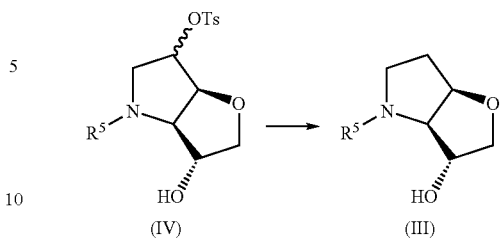

Preferably, this step involves treating a compound of formula (IV) with a metal triethylborohydride such as lithium, sodium or potassium.

In a more preferred embodiment the R$^5$ protecting group in compound (IV) is tert-butoxycarbonyl (Boc).

In a yet more preferred embodiment the process of the invention comprises the step of converting a compound of formula (IVa) into a compound of formula (III)

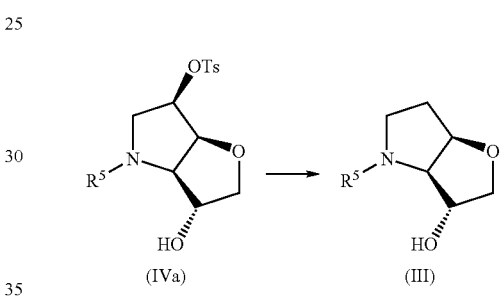

In one preferred embodiment the process of the invention comprises the step of converting a compound of formula (V) into a compound of formula (IV)

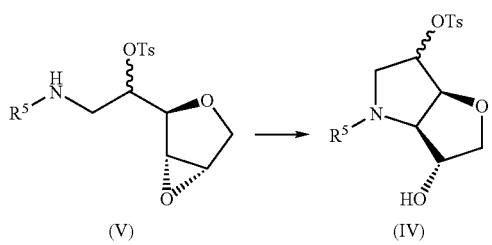

More preferably, the process comprises treating a compound of formula (V) with sodium hydride. Preferably, the reaction is carried out in THF.

In an alternative preferred embodiment of the invention, the intra-molecular cyclisation of compound (V) is induced by removal of the protecting group R$^5$. Preferably, for this embodiment, R$^5$ is benzyloxycarbonyl (Cbz), and the process comprises hydrogenating a compound of formula (V) in the presence of a palladium catalyst.

In one preferred embodiment the process of the invention comprises the step of converting a compound of formula (VI) into a compound of formula (V)

In one preferred embodiment, the oxidising agent is mCPBA.

In another preferred embodiment, the oxidising agent is a dioxirane.

The use of dioxiranes as oxidising agents is well documented in the literature [see (a) Hodgson, D. M. et al., Synlett, 310 (2002); (b) Adam, W. et al, Acc. Chem. Res. 22, 205, (1989); (c) Yang, D. et al, J. Org. Chem., 60, 3887, (1995); (d) Mello, R. et al, J. Org. Chem., 53, 3890, (1988); (e) Curci, R. et al, Pure & Appl. Chem., 67(5), 811 (1995); (f) Emmons, W. D. et al, J. Amer. Chem. Soc. 89, (1955)].

Preferably, the dioxirane is generated in situ by the reaction of $KHSO_5$ with a ketone. However, the oxidation step can also be carried out using an isolated dioxirane, for example a stock solution of the dioxirane formed from acetone.

More preferably, the dioxirane is generated in situ using Oxone®, which is a commercially available oxidising agent containing $KHSO_5$ as the active ingredient.

Thus, in one preferred embodiment, the claimed process involves the in situ epoxidation of a compound of formula (VI) using Oxone® (2 $KHSO_5 \cdot KHSO_4 \cdot K_2SO_4$) and a ketone co-reactant.

As mentioned above, the active ingredient of Oxone® is potassium peroxymonosulfate, $KHSO_5$ [CAS-RN 10058-23-8], commonly known as potassium monopersulfate, which is present as a component of a triple salt with the formula 2 $KHSO_5 \cdot KHSO_4 \cdot K_2SO_4$ [potassium hydrogen peroxymonosulfate sulfate (5:3:2:2), CAS-RN 70693-62-8; commercially available from DuPont]. The oxidation potential of Oxone® is derived from its peracid chemistry; it is the first neutralization salt of peroxymonosulfuric acid $H_2SO_5$ (also known as Caro's acid).

$$K^+ \; ^-O—S(=O)_2(—OOH) \quad \text{Potassium Monopersulfate}$$

Under slightly basic conditions (pH 7.5-8.0), persulfate reacts with the ketone co-reactant to form a three membered cyclic peroxide (a dioxirane) in which both oxygens are bonded to the carbonyl carbon of the ketone. The cyclic peroxide so formed then epoxidises the compound of formula VI by syn specific oxygen transfer to the alkene bond.

Preferably, the ketone is of formula (XIX)

wherein $R^a$ and $R^b$ are each independently alkyl, aryl, haloalkyl or haloaryl.

Where $R^a$ and/or $R^b$ are alkyl, the alkyl group may be a straight chain or branched alkyl group. Preferably, the alkyl group is a $C_{1-20}$ alkyl group, more preferably a $C_{1-15}$, more preferably still a $C_{1-12}$ alkyl group, more preferably still, a $C_{1-8}$ or $C_{1-6}$ alkyl group, more preferably a $C_{1-4}$ alkyl group.

Particularly preferred alkyl groups include, for example, methyl, ethyl, propyl, isopropyl, butyl, isobutyl, tert-butyl, pentyl and hexyl.

As used herein, the term "haloalkyl" refers to an alkyl group as described above in which one or more hydrogens are replaced by halo.

Where $R^a$ and/or $R^b$ are aryl, the aryl group is typically a $C_{6-12}$ aromatic group. Preferred examples include phenyl and naphthyl etc.

As used herein, the term "haloaryl" refers to an aryl group as described above in which one or more hydrogens are replaced by halo.

By way of example, the reaction of $KHSO_5$ (Oxone®) with a ketone of formula XVI would form a dioxirane of formula:

wherein $R^a$ and $R^b$ are as defined above.

More preferably, $R^a$ and $R^b$ are each independently alkyl or haloalkyl.

In a highly preferred embodiment, at least one of $R^a$ and $R^b$ is a haloalkyl, more preferably, $CF_3$ or $CF_2CF_3$.

In one preferred embodiment, $R^a$ and $R^b$ are each independently methyl or trifluoromethyl.

In one preferred embodiment of the invention, the ketone is selected from acetone and a 1,1,1-trifluoroalkyl ketone.

In a more preferred embodiment of the invention, the trifluoroalkyl ketone is 1,1,1-trifluoroacetone or 1,1,1-trifluoro-2-butanone, more preferably 1,1,1-trifluoro-2-butanone.

In one preferred embodiment the process of the invention comprises the step of converting a compound of formula (VII) into a compound of formula (VI)

Preferably the process comprises treating a compound of formula (VII) with tosyl chloride in pyridine. Alternatively the process comprises treating a compound of formula (VII) with tosyl chloride in dichloromethane and triethylamine.

In one preferred embodiment the process of the invention comprises the step of converting a compound of formula (VIII) into a compound of formula (VII)

where W is halogen or tosyl.

Preferably, this step comprises the steps of:

(a) reacting a compound of formula (VIII), where W is halogen or OTs, with aqueous ammonia and alcohol; and (b) converting the product formed in step (a) to a compound of formula (VII).

Preferably, steps (a) and (b) of the above process are a one-pot process.

In one particularly preferred embodiment, $R^5$ is benzyloxycarbonyl, and step (b) comprises treating the mixture formed in step (a) with benzyloxycarbonyl chloride.

Preferably, W is I, Br or OTs, more preferably, Br or OTs, even more preferably OTs.

Preferably, the alcohol is isopropyl alcohol or ethanol.

In one preferred embodiment of the invention, said compound of formula VIII is prepared from a compound of formula IX

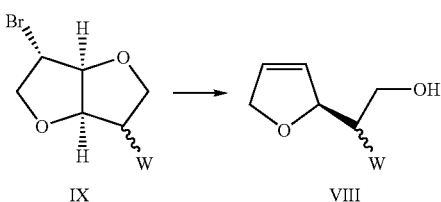

Preferably, the above process comprises treating said compound of formula IX with methyl lithium.

More preferably, compound of formula IX is compound 47 and compound of formula VIII is compound 14; or compound of formula IX is compound 46 and compound of formula VIII is compound 13. Treatment of monobromotosylates 46 or 47 with zinc dust at room temperature in organic/aqueous mixtures (most preferably an isopropanol, tetrahydrofuran, water, ammonium chloride mixture) provides alcohols 13 and 14 respectively in high yield. Additionally, completion of the one-pot conversion gives alcohols VIIa and VIIb with defined stereochemistry and in high yield.

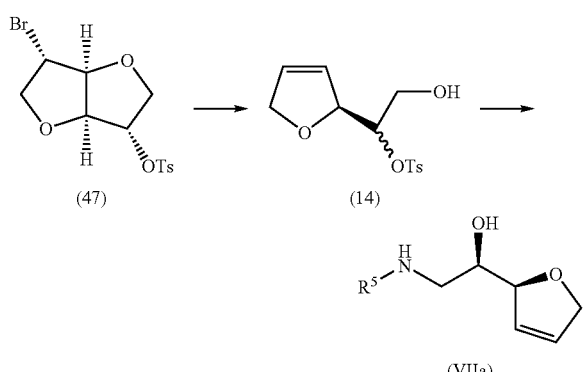

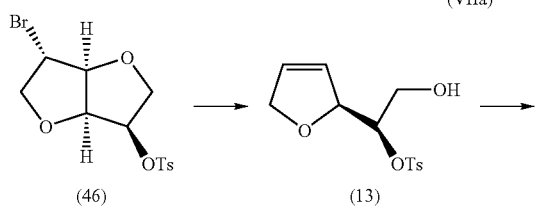

-continued

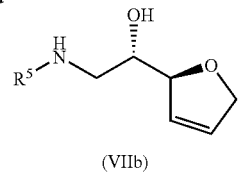

Commencing from the commercially available sugars isomannide and isosorbide, the present invention also provides facile preparation of monobromotosylates 46 and 47 One highly preferred preparation is shown below in Scheme 15

Scheme 15:

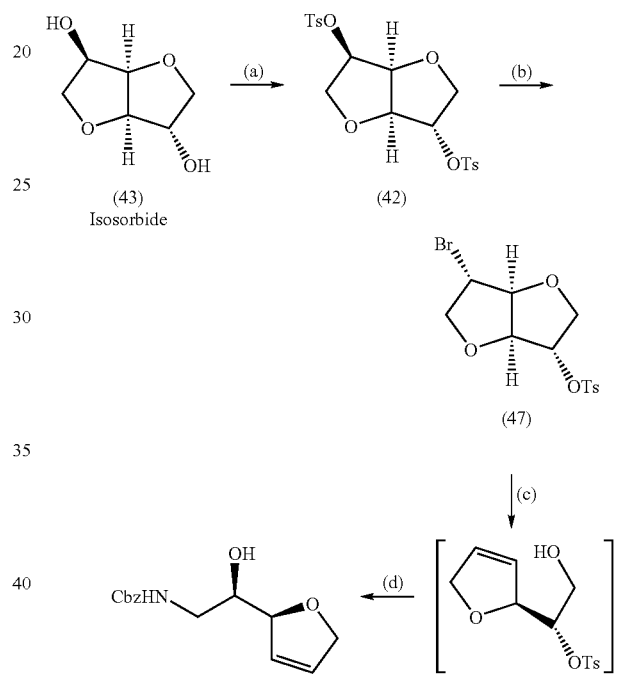

(a) TsCl, triethylamine, DCM, 25° C. → 50° C., 20 h under Ar; LiBr, DMSO, 110° C. → 120°C., 10 h under Ar, (c) Zn, $^i$PrOH, THF, $H_2O$, $NH_4Cl$, RT, 16 h; (d) (i) $NH_4OH$, $NH_3$ in $^i$PrOH, 75° C., 16 h; (ii) Cbz-Cl, $Na_2CO_3$, dioxane, water.

Isosorbide (43) is converted to the di-tosylate (42) which is obtained following recrystallisation from methanol in 97% yield. Mono-bromination is effected by 2.5 eq lithium bromide in DMSO (or DMF) with temperature control 110° C.→120° C. The product bromide is isolated following extractive work-up and purification either by column chromatography (74%) or attractive for large scale by recrystallisation from methanol giving a first crop of 55% plus mother liquors containing good quality material that may be pooled from batch runs and purified later. Thus, preparation of monobromotosylate (47) with defined stereochemistry by methods in Scheme 15 is attractive for large scale applications. Treatment of monobromotosylate (47) with zinc dust at room temperature in organic/aqueous mixtures (most preferably an isopropanol, tetrahydrofuran, water, ammonium chloride mixture) provides alcohol (14) which is derivatised as the Cbz compound (18) through one pot conversion.

Scheme 16:

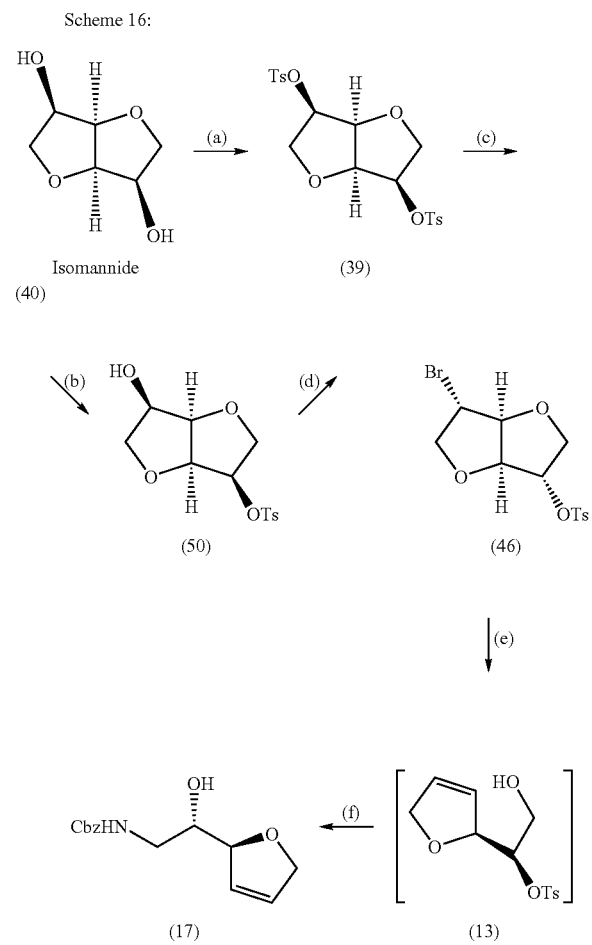

(a) 2.2 eq. TsCl, KOH (aq), DCM, CCl₄, 0° C., 24 h under Ar; (b) (i) 0.5 eq TsCl, KOH (aq), DCM, CCl₄, 0° C., 7 h under Ar or (ii) 1.0 eq TsCl, pyridine, 0° C. → RT, 1 h; (c) LiBr, DMF, 100° C., 27 h; (d) CBr₄, Ph₃P, pyridine, 65° C., 2 h under Ar; (e) Zn, ⁱPrOH, THF, H₂O, NH₄Cl, RT, 16 h; (f) (i) NH₄OH, NH₃ in ⁱPrOH, 75° c., 16 h; (ii) Cbz-Cl, Na₂CO₃, dioxane, water.

Treatment of isomannide (40) (Scheme 16) with tosylchloride (2.2 eq) in a bi-phasic potassium hydroxide/dichloromethane/carbon tetrachloride mixture at 0° C. gives ditosylate (39) in 48% yield following simple filtration and trituration with methanol. Alternatively, treatment of isomannide (40) with tosylchloride (0.5 eq) in a bi-phasic potassium hydroxide/dichloromethane/carbon tetrachloride mixture at 0° C. gives monotosylate in 38% yield following simple extraction and re-crystallisation from carbon tetrachloride (conditions as described in U.S. Pat. No. 6,858,632). Although the monotosylate can be obtained in higher yield by treatment of isomannide (40) with tosylchloride in pyridine, purification currently requires column chromatography which may becomes undesirable at large scale. Monobromotosylate (46) may then be prepared by treatment of ditosylate (39) with lithium bromide in DMF (29% yield following chromatography) or by treatment of monotosylate under Mitsunobu conditions with carbon tetrabromide (63% yield following chromatography). Treatment of monobromotosylate (46) with zinc dust at room temperature in organic/aqueous mixtures (most preferably an isopropanol, tetrahydrofuran, water, ammonium chloride mixture) provides alcohol (13) which is derivatised as the Cbz compound (17) through one pot conversion.

In one highly preferred embodiment of the invention, the 5,5-bicylic core is prepared in accordance with the steps set forth in Scheme 1 below:

The alcohol functionality of (18) may be derivatised as the para-toluene sulphonate (Ts) giving (R)-2-(benzyloxycarbonylamino)-1-((S)-2,5-dihydrofuran-2-yl)ethyl 4-methylbenzenesulfonate (32b) which proceeds through the anti-epoxide (R)-2-(benzyloxycarbonylamino)-1-((1S,2S,5S)-3,6-dioxabicyclo[3.1.0]hexan-2-yl)ethyl 4-methylbenzenesulphonate (33b). Hydrogenation of tosylate (33b) provides free amine that undergoes intramolecular cyclisation. Urethane protection of the secondary amine of the bicyclic intermediate gives (3R,3aR,6R,6aS)-benzyl 3-hydroxy-6-(tosyloxy) tetrahydro-2H-furo[3,2-b]pyrrole-4(5H)-carboxylate (34b) or (3R,3aR,6R,6aS)-tert-butyl 3-hydroxy-6-(tosyloxy)tetrahydro-2H-furo[3,2-b]pyrrole-4(5H)-carboxylate (35b). An analogous reaction scheme can be applied to the enantiomer of (18), namely, benzyl(S)-2-((S)-2,5-dihydrofuran-2-yl)-2-hydroxyethyl carbamate (17), proceeding through the analogous anti-epoxide (S)-2-(benzyloxycarbonylamino)-1-((1S,2S,5S)-3,6-dioxabicyclo[3.1.0] hexan-2-yl)ethyl 4-methylbenzenesulphonate.

Subsequent treatment of tosylate (35b) with super-hydride (for general refs. see (a) Brown, H. C., et al, J. Org. Chem., 45(1), 1-12, 1980; (b) Krishnamurthy, S and Brown, H. C., J. Org. Chem., 41(18), 3064-3066, 1976) reduces out the tosyl group giving the saturated bicycle intermediate. Advantageously, the epoxidation to give the desired anti-epoxide is directed by the presence of the tosylate group whilst only modest stereoselectivity can be achieved for the corresponding saturated alkene. Thus, although this route to the 6-unsubstituted derivatives involves additional synthetic steps, the stereoselectivity of the epoxidation is controlled to allow much higher yields of the desired anti-epoxide.

Scheme 1:

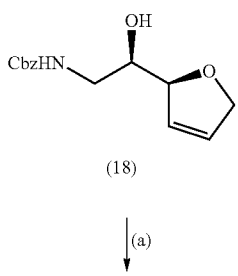

(18)

(a)

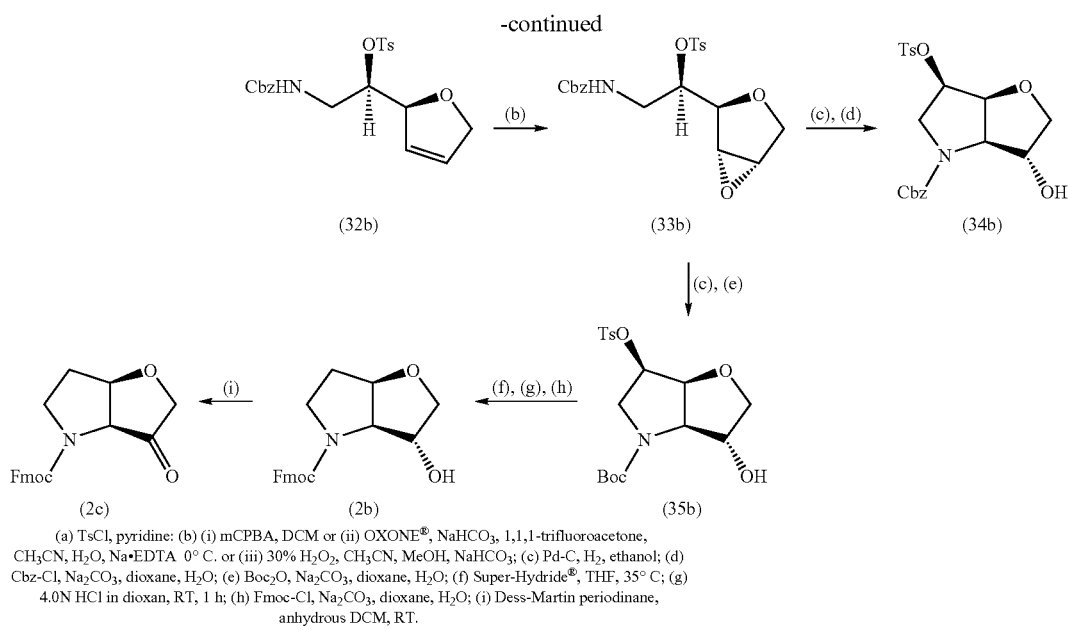

(a) TsCl, pyridine; (b) (i) mCPBA, DCM or (ii) OXONE®, NaHCO₃, 1,1,1-trifluoroacetone, CH₃CN, H₂O, Na•EDTA 0° C. or (iii) 30% H₂O₂, CH₃CN, MeOH, NaHCO₃; (c) Pd-C, H₂, ethanol; (d) Cbz-Cl, Na₂CO₃, dioxane, H₂O; (e) Boc₂O, Na₂CO₃, dioxane, H₂O; (f) Super-Hydride®, THF, 35° C; (g) 4.0N HCl in dioxan, RT, 1 h; (h) Fmoc-Cl, Na₂CO₃, dioxane, H₂O; (i) Dess-Martin periodinane, anhydrous DCM, RT.

In an alternative preferred embodiment the process of the invention comprises the step of converting a compound of formula (XII), wherein PG₂ is a protecting group, into a compound of formula (IIa)

In one highly preferred embodiment, the reaction proceeds via the process illustrated in Scheme 2 below.

Scheme 2:

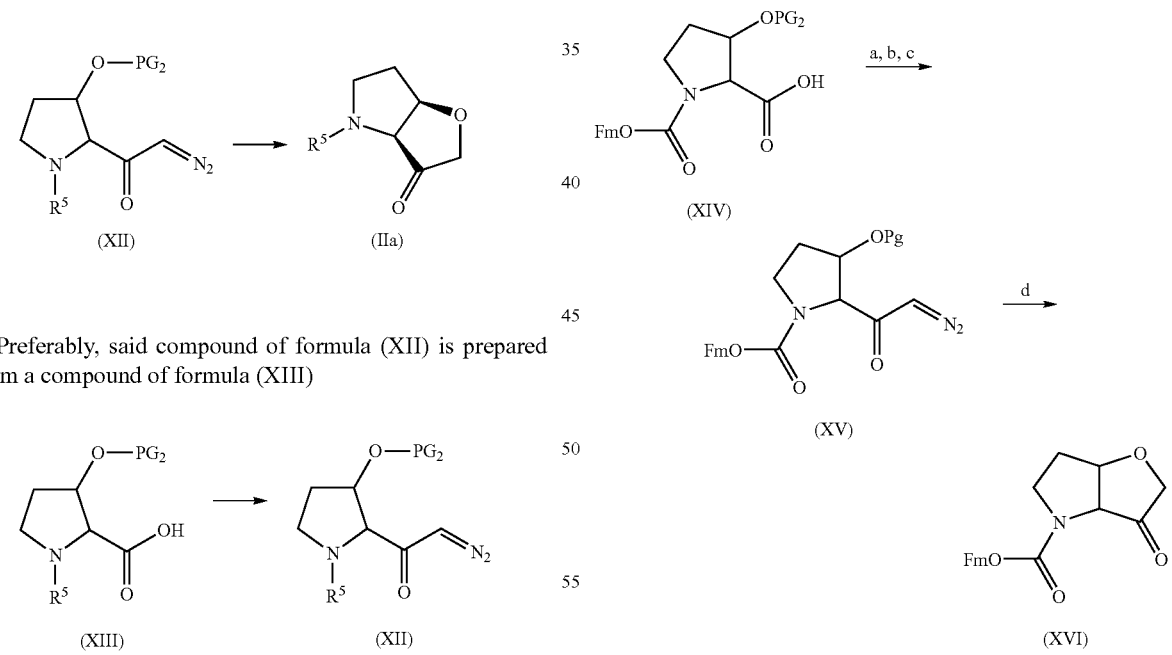

(a) ⁱBuOCOCl, NMM, DCM, -15° C., 10 mins, under argon.
(b) Diazomethane in diethyl ether, -15° C. to RT over 1 hr, then o/n.
(c) Acetic acid (d) LiCl (10 eq) in 80% aq acetic acid, 5° C. to RT over 1 hr.

Preferably, said compound of formula (XII) is prepared from a compound of formula (XIII)

In one preferred embodiment, protecting group R⁵ is selected from benzyloxycarbonyl, tert-butoxycarbonyl, fluoren-9-ylmethoxycarbonyl.

In one particularly highly preferred embodiment of the invention, R⁵ is tert-butoxycarbonyl (Boc) or fluoren-9-ylmethoxycarbonyl (Fmoc).

Preferably, PG₂ is tert-butyl ether.

FmOC(O) denotes the well known amine protecting group 9-fluorenyl methoxycarbonyl (Fmoc, see Atherton, E. and Sheppard, R. C., 1989) and PG₂ denotes either a free hydroxyl or an hydroxyl protecting group such as tert-butyl ether. Although formation of the diazoketone is clearly observed at 1 hr reaction, an overall improvement in isolated yield is obtained by leaving the reaction with ethereal diazomethane for 24 hr.

Considering step (a), synthesis may commence from suitably protected 3-hydroxyproline (XIV), which are accessible through a variety of literature methods e.g. (a) Heffner, R. J., et al, *J. Am. Chem. Soc.*, 114, 10181-10189, 1992; (b) Hughes, P. Cardy, J., *J. Org. Chem.*, 54, 3260-3264, 1989, (c) Heffner, R. J., Jouille, M. M., *Tet. Lett,* 30, 7021-7024, 1989, (d) Ewing, W. R., Jouille, M. M., *Heterocycles,* 27, 2843-2850, 1988. (e) Kolodziej, S. A., Marshall, G. R., *Int. J. Pept. Prot. Res.,* 48, 274-280, 1996, (f) Evans, D. A., Weber, A, E., *J. Am. Chem. Soc,* 109, 7151-7157, 1987, (g) Langlois, N., Rakotondradany, F., *Tetrahedron,* 56, 2437-2448, 2000, (h) Sugisaki, C. H., et al, *Tet. Lett.,* 39, 3413-3416, 1998, (i) Greck, C., et al, *Tet. Lett.,* 37, 2031-, 1996, 0) Agami, C., et al, *Tet. Lett.,* 37, 4001-, 1996.

Activation of the suitably protected 3-hydroxyproline (XIV) via isobutyl chloroformate mixed anhydride, followed by condensation with diazomethane, yields the diazomethylketone intermediates (XV). Treatment of diazomethylketone intermediate (XV) with lithium chloride in aqueous acetic acid provides the protected tetrahydrofuro[3,2-b]pyrrol-3-one (XVI).

Synthesis of Compounds of Formula (I)

To those skilled in the practices of organic chemistry, compounds of general formula (I) may be readily synthesised by a number of chemical strategies, performed either in solution or on the solid phase (see Atherton, E. and Sheppard, R. C. In '*Solid Phase Peptide Synthesis: A Practical Approach*', Oxford University Press, Oxford, U.K. 1989, for a general review of solid phase synthesis principles), or a combination thereof.

Compounds of general formula (I) may be conveniently considered as a combination of three building blocks (P1, P2 and P3) that respectively occupy the S1, S2 and S3 binding sites of the protease (see Berger, A. and Schechter, I., *Philos. Trans. R. Soc. Lond. [Biol.],* 257, 249-264, 1970 for a description of the designation of enzyme S-subsites and substrate P-subsites within enzyme-substrate or enzyme-inhibitor complexes). The notional concepts of P1, P2 and P3 are used herein for convenience only and the above-mentioned compounds are intended to be within the scope of the invention regardless of binding mode.

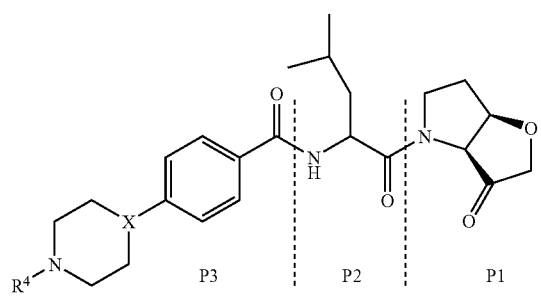

A suitably protected and/or activated building block may then be prepared and subsequently chemically bonded (coupled) together with other building blocks to provide compounds of general formula (I).

Compounds of formula (I) may be prepared: (1) by the stepwise addition of P3 and P2 to the bicyclic tetrahydrofuro[3,2-b]pyrrol-3-one core; or (2) by reaction of the bicyclic tetrahydrofuro[3,2-b]pyrrol-3-one core with a P3-P2 precursor molecule; or (3) by introducing the P3-P2 group prior to formation of the bicyclic tetrahydrofuro[3,2-b]pyrrol-3-one core, i.e. prior to the oxidation step or prior to the intramolecular cyclisation step.

Thus, alternative orders of coupling of the building blocks are possible, for example P2+P1→P2-P1 then addition of P3→P3-P2-P1 or P3+P2→P3-P2 then addition to P1→P3-P2-P1. Within each of these combinations each of the P1, P2 or P3 building blocks may contain additional alternative functionalities that are further transformed following coupling to give the final compound. For example the ketone functionality of the P1 building block may be protected as a ketal during coupling of building blocks and transformed to the final ketone by hydrolysis following completion of the coupling reactions. Alternatively, the ketone functionality of the P1 building block may be initially introduced via a lower oxidation state such as the corresponding alcohol and following completion of the coupling reactions be re-introduced by oxidation of the alcohol. Alternatively, the ketone functionality of the P1 building block may be protected through a semi-carbazone suitable for solid phase synthesis (e.g. see WO 02/057270 and references cited therein) and following completion of the coupling reactions released from the solid phase by acidolytic reaction.

The chemical bond formed by coupling of the building blocks is a secondary amide (P3-P2) or a tertiary amide (P2-P1) that are formed through reaction of an activated carboxylic acid with a primary and secondary amine respectively. Many methods are available for activation of a carboxylic acid prior to coupling to an amine and in principle, any of these methods may be used herein. Typical carboxylic acid activation methods are exemplified but not restricted to the azide method, mixed anhydride method (e.g. via isobutylchloroformate), carbodiimide methods (e.g. via dicyclohexylcarbodiimide, diisopropylcarbodiimide, 1-ethyl-3-(3'-dimethylamino propyl)carbodiimide), active ester method (e.g. via p-nitrophenyl ester, N-hydroxysuccinic imido ester, pentafluorophenyl ester), uronium method (e.g. via addition of HBTU, PyBop, BOP), carbonyldiimidazole method or via pre-formation of acyl fluorides or acyl chlorides. In some instances the coupling reaction may be enhanced by the addition of a further activation catalyst such as 1-hydroxybenzotriazole, or 4-dimethylaminopyridine. A general description of carboxylic acid activation techniques and the use of activation additives may be found in Bodanszky, M. 'Principles of Peptide Synthesis', $2^{nd}$ rev. ed., Springer-Verlag, Berlin, 1993 and references cited therein.

The α-amino group of the P2 aminoacid building block is usually protected during coupling reactions to the P1 building block to avoid the formation of undesired self-condensation products. The art of α-amino protection is well known in peptide chemistry (e.g. see Bodanszky, M. 'Principles of Peptide Synthesis', $2^{nd}$ rev. ed., Springer-Verlag, Berlin, 1993 and references cited therein) and example protection groups include, but are not limited to, 9-fluorenylmethoxycarbonyl (Fmoc), tert-butoxycarbonyl (Boc), benzyloxycarbonyl (Cbz), allyloxycarbonyl (Alloc) and trichloroethoxycarbonyl (Treoc). The Fmoc group is particularly well suited for solid phase syntheses (e.g. see Atherton, E.; Sheppard, R. C. in 'Solid Phase Peptide Synthesis A Practical Approach', IRL Press, Oxford, U.K., 1989) typically being removed by treatment with 20% v/v piperidine in dimethylformamide or 1% v/v 1,8-diazabicyclo[5.4.0]undec-7-ene in dimethylformamide. The Boc group is particularly well suited to solution phase syntheses typically being removed by treatment with trifluoroacetic acid based mixtures or HCl in dioxane or ethyl acetate. The Cbz group is also particularly well suited for solution phase syntheses typically being removed by catalytic hydrogenation with hydrogen and palladium catalysis or by treatment with HBr in acetic acid. Once the coupling sequence is complete, any protecting groups are removed in whatever manner is dictated by the choice of protecting groups (for a general description of protecting groups and their respective stabilities and methods of removal see Greene, T. W. and Wuts, P. G. M. 'Protective Groups in Organic Synthesis' John Wiley and Sons, New York, 1991 and references therein).

In the simplest example, the entire left hand portion of a compound of general formula (I) (i.e. P3–P2) as the carboxylic acid can be prepared in solution by traditional organic chemistry methods and coupled to ketone, alcohol or ketal intermediates such as compounds (IIb), (IIc) and (IId). Then oxidation of the alcohol intermediate (e.g. Dess-Martin periodinane in DCM) or acidolytic cleavage of the ketal intermediate provides compounds of general formula (I). The alcohol oxidation route is particularly useful when the compound of general formula (I) contains a substituent that is labile to trifluoroacetic acid, this being the final reagent used in each of the solid phase syntheses.

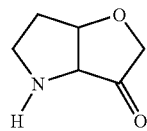
(IIb)

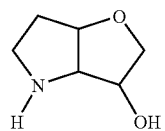
(IIc)

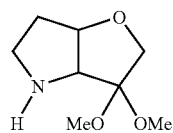
(IId)

Examples of these different coupling tactics have been detailed previously (see (i) Quibell, M. et. al., *Bioorg. Med. Chem.* 13, 609-625, 2005. (ii) Wang, Y. et. al., *Bioorg. Med. Chem. Lett.* 15, 1327-1331, 2005) and the optimum synthetic route is dependant upon the specific substituent combinations of the target compound of general formula (I).

In more detail, one preferred strategy for the synthesis of compounds of general formula (I) comprises:—

(a) Preparation of an appropriately functionalised and protected bicyclic ketone or bicyclic alcohol building block in solution;

(b) Attachment of the building block (a) to the solid phase through a linker that is stable to the conditions of synthesis, but readily labile to cleavage at the end of a synthesis (see James, I. W., *Tetrahedron,* 55(Report No 489), 4855-4946, 1999, for examples of the 'linker' function as applied to solid phase synthesis);

(c) Solid phase organic chemistry (see Brown, R. D. *J. Chem. Soc., Perkin Trans.* 1, 19, 3293-3320, 1998), to construct the remainder of the molecule;

(d) Compound cleavage from the solid phase into solution; and (e) Cleavage work-up and compound analysis.

A second strategy for the synthesis of compounds of general formula (I) comprises:—

(a) Preparation of an appropriately functionalised and protected bicyclic intermediate building block in solution. Preferred protecting groups for solution phase chemistry are the 9-fluorenylmethoxycarbonyl (Fmoc), Nα-tert-butoxycarbonyl (Boc), Nα-benzyloxycarbonyl (Cbz) and Nα-allyloxycarbonyl group (Alloc).

(b) Standard organic chemistry methods for the conversion of building block obtained in step (a) towards compounds of general formula (I).

As mentioned above, in one preferred embodiment of the invention, compounds of formula (I) may be prepared using conventional solution phase chemistry, for example, as described in Quibell, M et al, Bioorg. Med. Chem., 13, 609-625, 2005 (see in particular, Schemes 3 and 4). The solution phase strategy is attractive in being able to generate larger quantities of preferred analogues, typically on a multi-gram to multi-kilogram scale.

In an alternative preferred embodiment of the invention, compounds of formula (I) may be prepared using conventional solid phase chemistry, for example, as described in Quibell M, et al Bioorg. Med. Chem., 12, 5689-5710, 2004, see in particular, Scheme 3 and Section 3.2, and references cited therein; and Bioorg. Med. Chem., 13, 609-625, 2005, see Scheme 5 and Section 2.2, and references cited therein). The solid phase strategy is attractive in being able to generate many thousands of analogues, typically on a 5-100 mg scale, through established parallel synthesis methodologies (e.g. see (a) Bastos, M.; Maeji, N.J.; Abeles, R. H. *Proc. Natl. Acad. Sci. USA,* 92, 6738-6742, 1995).

The synthetic strategy is based on reversible anchorage of the ketone functionality via a hydrazide linker bond using general multipin techniques previously described in the art (Watts J. et al, Bioorg. Med. Chem. 12(11), 2903, 2004; Quibell M., et al, Bioorg. Med. Chem. 5689-5710, 2004; Grabowksa U. et al, J. Comb. Chem. 2000, 2(5), 475).

Compounds of formula (II) may be utilised in a solid phase synthesis of inhibitor molecules (I). The solid phase linkage of an aldehyde or ketone, has previously been described by a variety of methods (e.g. see (a) James, I. W., 1999, (b) Lee, A., Huang, L., Ellman, J. A., *J. Am. Chem. Soc,* 121(43), 9907-9914, 1999, (c) Murphy, A. M., et al, J. Am. Chem. Soc, 114, 3156-3157, 1992). A suitable method amenable to the reversible linkage of an alkyl ketone functionality is through a combination of the previously described chemistries. The semicarbazide, 4-[[(hydrazinocarbonyl)amino]methyl]cyclohexane carboxylic acid. trifluoroacetate (Murphy, A. M., et al, J. Am. Chem. Soc, 114, 3156-3157, 1992), may be utilised as illustrated in Scheme 3, exemplified by linkage of the tetrahydrofuro[3,2-b]pyrrol-3-one (II; $R^5$=Fmoc).

Scheme 3:

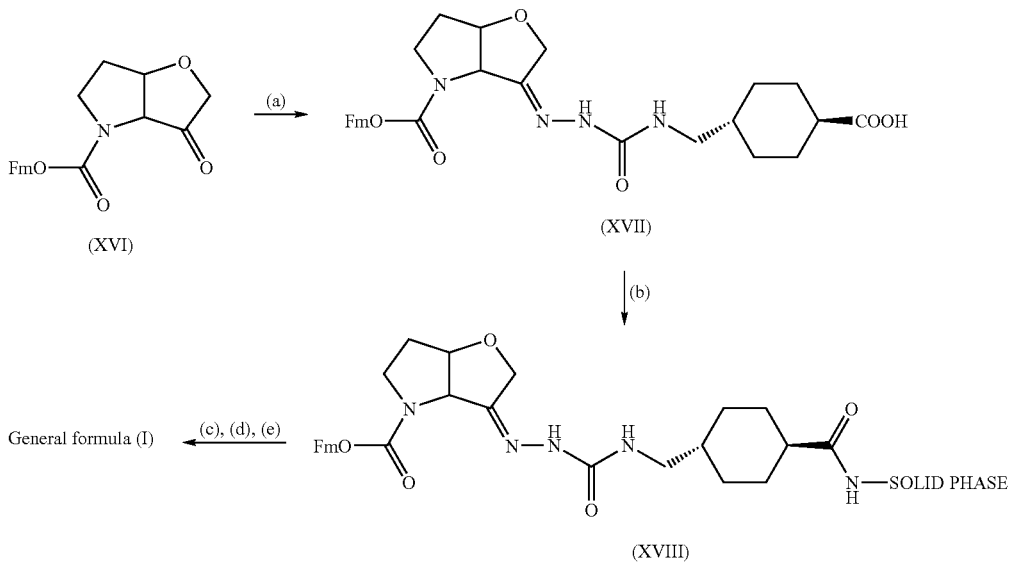

(a) (XVI) in 90% EtOH/H₂O/1.5 eq NaOAc/4-[[(hydrazinocarbonyl)-amino]methyl]-cyclohexane carboxylic acid. trifluoroacetate (20), 2 hr reflux. (b) 3 eq construct (XVII)/3 eq HBTU/3 eq HOBt/6 eq NMM, NH₂-SOLID PHASE, DMF, RT, o/n. (c) 20% piperidine/DMF, 30 mins. (d) Range of chemistries to introduce P3-P2 (e) TFA/H₂O (95:5, v/v), RT, 2 hr.

Construct (XVII) is prepared through reaction of the linker molecule and the tetrahydrofuro[3,2-b]pyrrol-3-one II (R⁵=Fmoc) by refluxing in aqueous ethanol/sodium acetate. Standard solid phase techniques (e.g. see Atherton, E. and Sheppard, R. C., 1989) are used to anchor the construct to an amino-functionalised solid phase through the free carboxylic acid functionality of (XVII), providing the loaded construct (XVIII). Loaded construct (XVIII) be reacted with a wide range of carboxylic acids available commercially or in the literature, to introduce the left-hand portion 'P3–P2'.

The present invention is further described by way of example.

EXAMPLES

General Procedures

Solvents were purchased from ROMIL Ltd, U.K. at SpS or Hi-Dry grade unless otherwise stated. $^1$H NMR and $^{13}$C NMR were obtained on a Bruker DPX400 (400 MHz $^1$H frequency and 100 MHz $^{13}$C frequency; QXI probe) or Bruker Avance 500 MHz (TXI probe with ATM) in the solvents indicated. Chemical shifts are expressed in parts per million (δ) and are referenced to residual signals of the solvent. Coupling constants (J) are expressed in Hz. All analytical HPLC were obtained on Phenomenex Jupiter $C_4$, 5μ, 300 Å, 250×4.6 mm, using mixtures of solvent A (0.1% aq trifluoroacetic acid (TFA)) and solvent B (90% acetonitrile/10% solvent A) on automated Agilent systems with 215 and/or 254 nm UV detection. Unless otherwise stated a gradient of 10 to 90% B in A over 25 min at 1.5 mL/min was performed for full analytical HPLC. HPLC-MS analysis was performed on an Agilent 1100 series LC/MSD, using automated Agilent HPLC systems, with a gradient of 10 to 90% B in A over 10 min on Phenomenex Luna $C_8$, 5μ, 300 Å, 50×2.0 mm at 0.6 mL/min. Semi-preparative HPLC purification was performed on Phenomenex Jupiter $C_4$, 5μ, 300 Å, 250×10 mm, using a gradient of 10 to 90% B in A over 25 min at 4 mL/min on automated Agilent systems with 215 and/or 254 nm UV detection. Flash column purification was performed on silica gel 60 (Merck 9385) or using isolute SPE flash silica columns (Biotage, Hengoed, UK).

Preparation of Benzyl(R)-2-((S)-2,5-dihydrofuran-2-yl)-2-hydroxyethyl Carbamate (18)

(i) Preparation of (3R,3aS,6S,6aS)-Hexahydrofuro[3,2-b] furan-3,6-diyl bis(4-methylbenzenesulfonate) (42). A stirred solution of p-toluenesulfonyl chloride (57.4 g, 301 mmol) and isosorbide (43) (20 g, 137 mmol) in pyridine (315 mL) was heated at 95° C. for 4.5 hours under an atmosphere of argon then stood at ambient temperature for 16 hours before being poured onto iced-water (1 L). The aqueous was extracted with dichloromethane (2×500 mL), then the combined organic layers were washed with water (2×500 mL), then dried (Na₂SO₄), filtered then reduced in vacuo to leave a viscous oil (65.22 g). The oil was crystallized from hot methanol (350 mL). The white solid was collected by filteration in vacuo, then washed with methanol (100 mL) and dried in vacuo to obtain ditosylate (42) as a white solid (45.87 g, 74%). TLC ($R_f$=0.30, EtOAc:heptane 2:3), analytical HPLC single main peak, $R_t$=20.219 min., HPLC-MS 455.1 [M+H]⁺, 931.2 [2M+Na]⁺, $[α]_D^{20}$+57.2° (c=10.2, CHCl₃); $δ_H$ (500 MHz, CDCl₃) 2.44 (6H, s, CH₃), 3.68 (1H, dd, J=9.80 and 6.46 Hz, CH₂), 3.82-3.87 (2H, m, CH₂), 3.94 (1H, d, J=11.28 Hz, CH₂), 4.46 (1H, d, J=4.44 Hz, CHCHOTs), 4.58 (1H, t, J=4.74 Hz, CHCHOTs), 4.82-4.86 (2H, m, CHOTs), 7.32-7.36 (4H, m, aromatic CH₃CCH), 7.74-7.80 (4H, m, aromatic OSO₂CCH).

Alternative Preparation of (3R,3aS,6S,6aS)-Hexahydrofuro[3,2-b]furan-3,6-diyl bis(4-methylbenzenesulfonate) (42). Triethylamine (123.2 mL, 876 mmol) was added dropwise to a stirred solution of p-toluenesulfonyl chloride (156.6 g, 822 mmol) and isosorbide (43) (40 g, 274 mmol) in dichloromethane (600 mL) over 15 minutes. The mixture was stirred at 25° C. for 16 hours then at 50° C. for 4 hours before diluting with dichloromethane (1 L). The organic layer was washed with water (2×1 L), then dried (Na$_2$SO$_4$), filtered then reduced in vacuo to leave a viscous oil. The oil was crystallized from hot methanol (600 mL) to obtain ditosylate (42) as a white solid (120.1 g, 97%). $[\alpha]_D^{15}$+56.3° (c=11.2, CHCl$_3$).

(ii) Preparation of (3S,3aS,6S,6aS)-6-Bromohexahydrofuro[3,2-b]furan-3-yl 4-methylbenzenesulfonate (47). Lithium bromide (9.6 g, 110.1 mmol) was added to a stirred solution of ditosylate (42) (20.0 g, 44.05 mmol) in dimethylformamide (100 mL) under an atmosphere of argon. The mixture was heated at 110° C. for 5 hours then stood at ambient temperature for 3 days, then heated at 90° C. for 3.5 hours. The mixture was diluted with water (250 mL) extracted with tert-butyl methyl ether (4×125 mL) then the organic phase washed with water (3×125 mL), brine (125 mL), dried (MgSO$_4$), filtered and reduced in vacuo to leave a brown oil (16.8 g). Flash chromatography over silica, eluting with ethyl acetate:heptane mixtures 0:100 to 30:70 gave bromotosylate (47) (11.88 g, 74%) as a pale yellow solid. TLC (R$_f$=0.20, EtOAc:heptane 1:3); analytical HPLC main peak, R$_t$=18.050 min; HPLC-MS 381.0/383.0 [M+H$_2$O+H]$^+$, 385.0/387.0 [M+Na]$^+$; $[\alpha]_D^{18}$+51.0° (c=5.0, CHCl$_3$); $\delta_H$ (500 MHz, CDCl$_3$) 2.45 (3H, s, CH$_3$), 3.84 (1H, dd, J=11.19 and 3.51 Hz, CH$_2$), 4.05-4.15 (3H, m, CH$_2$), 4.28 (1H, d, J=3.40 Hz, CHBr), 4.78 (1H, d, J=3.37 Hz, CHCH), 4.84 (1H, d, J=3.42 Hz, CHOTs), 4.90 (1H, d, J=3.37 Hz, CHCH), 7.36 (2H, brd, J=7.98 Hz, aromatic CH$_3$CCH), 7.79 (2H, brd, J=8.32 Hz, aromatic OSO$_2$CCH).

Alternative preparation of (3S,3aS,6S,6aS)-6-Bromohexahydrofuro[3,2-b]furan-3-yl 4-methylbenzenesulfonate (47). Lithium bromide (19.2 g, 220.2 mmol) was added to a stirred solution of ditosylate (42) (40.0 g, 88.1 mmol) in dimethyl sulfoxide (200 mL) under an atmosphere of argon. The mixture was heated at 110° C. for 8 hours then at 120° C. for 1.75 hours. The mixture was diluted with water (500 mL) then extracted with tert-butyl methyl ether (4×250 mL). The organic phase was washed with water (3×250 mL) then brine (250 mL), dried (MgSO$_4$), filtered and reduced in vacuo to leave an orange solid. Recrystallisation from methanol (100 mL) gave bromotosylate (47) (17.47 g, 55%) as a pale yellow solid. $[\alpha]_D^{15}$+49.5° (c=11.7, CHCl$_3$).

(iii) Preparation of (S)-1-((S)-2,5-Dihydrofuran-2-yl)-2-hydroxyethyl 4-methyl benzenesulfonate (14). Ammonium chloride (20 mg, 0.37 mmol) then zinc dust (20 mg, 0.31 mmol) were added to a solution of bromotosylate (47) (100 mg, 0.28 mmol) in ethanol (1.5 mL) under argon. The mixture was stirred for 16 hours before filtering the suspension through celite in vacuo. The filter cake was washed with ethanol (20 mL) then the filtrate reduced in vacuo to leave a residue (111 mg). Flash chromatography over silica, eluting with ethyl acetate:heptane mixtures 20:80 to 40:60 gave alcohol (14) (53 mg, 68%) as a white solid. TLC (R$_f$=0.15, EtOAc:heptane 1:2); analytical HPLC main peak, R$_t$=12.543 min; HPLC-MS 285.1 [M+H]$^+$, 302.1, 591.2 [2M+Na]$^+$; $[\alpha]_D^{15}$−86.8° (c=5.3, CHCl$_3$); $\delta_H$ (500 MHz, CDCl$_3$) 2.12 (1H, brs, OH), 2.44 (3H, s, aryl-CH$_3$), 3.77 (2H, d, J=4.85 Hz, CH$_2$OH), 4.54-4.58 (3H, m, CH$_2$OCH), 4.94-4.98 (1H, m, CHOTs), 5.64-5.67 and 5.97-6.00 (2H total, m, CH$_2$CH=CH), 7.33 (2H, brd, J=8.23 Hz, aromatic CH$_3$CCH), 7.79 (2H, brd, J=8.31 Hz, aromatic OSO$_2$CCH); $\delta_C$ (125 MHz, CDCl$_3$) 21.660 (CH$_3$), 62.303 (CH$_2$OH), 75.940 (OCH$_2$CH=), 82.720 and 85.221 (OCHCHOTs), 124.792, 127.977, 129.479 and 129.749 (OCH$_2$CH=CCH and aromatic CH), 133.496 (CHOSO$_2$C quaternary), 144.973 (CH$_3$C quaternary).

Alternative preparation of (S)-1-((S)-2,5-Dihydrofuran-2-yl)-2-hydroxyethyl 4-methyl benzenesulfonate (14). Ammonium chloride (200 mg, 3.7 mmol) then zinc dust (200 mg, 3.1 mmol) were added to a suspension of bromotosylate (47) (1 g, 2.75 mmol) in propan-2-ol (15 mL) under argon. The mixture was stirred for 16 hours before filtering the suspension through celite in vacuo. The filter cake was washed with propan-2-ol (20 mL) then the filtrate reduced in vacuo to leave a residue (1.43 g). Flash chromatography over silica, eluting with ethyl acetate:heptane mixtures 20:80 to 50:50 gave alcohol (14) (566 mg, 72%) as a white solid. $[\alpha]_D^{16}$−85.8° (c=10.2, CHCl$_3$).

Alternative preparation of (S)-1-((S)-2,5-Dihydrofuran-2-yl)-2-hydroxyethyl 4-methyl benzenesulfonate (14). A solution of ammonium chloride (200 mg, 3.7 mmol) in water (2.5 mL) then zinc dust (200 mg, 3.1 mmol) were added to a solution of bromotosylate (47) (1 g, 2.75 mmol) in tetrahydrofuran (10 mL) under argon. The mixture was stirred for 16 hours before filtering the suspension through celite in vacuo. The filter cake was washed with tert-butyl methyl ether (20 mL). Water (20 mL) and brine (20 mL) were added to the filtrate then the organic phase separated. The aqueous layer was extracted with tert-butyl methyl ether (20 mL) then the combined organic phase was washed with brine (20 mL), dried (MgSO$_4$), filtered and reduced in vacuo to leave a residue (0.82 g). Flash chromatography over silica, eluting with ethyl acetate:heptane mixtures 20:80 to 50:50 gave alcohol (14) (544 mg, 70%) as a white solid. $[\alpha]_D^{15}$−86.1° (c=10.8, CHCl$_3$).

Alternative preparation of (S)-1-((S)-2,5-Dihydrofuran-2-yl)-2-hydroxyethyl 4-methyl benzenesulfonate (14). A solution of ammonium chloride (200 mg, 3.7 mmol) in water (2.5 mL) then zinc dust (200 mg, 3.1 mmol) were added to a solution of bromotosylate (47) (1 g, 2.75 mmol) in tetrahydrofuran (10 mL) and propan-2-ol (5 mL) under argon. The mixture was stirred for 16 hours before filtering the suspension through celite in vacuo. The filter cake was washed with diethyl ether (20 mL). Hydrochloric acid (1M, 20 mL) was added to the filtrate then the organic phase separated. The aqueous layer was extracted with diethyl ether (20 mL) then the combined organic phase was washed with brine (20 mL), then dried (MgSO$_4$), filtered and reduced in vacuo to leave a residue (1.06 g). Flash chromatography over silica, eluting with ethyl acetate:heptane mixtures 20:80 to 50:50 gave alcohol (14) (528 mg, 68%) as a white solid. $[\alpha]_D^{15}$−82.7° (c=11.3, CHCl$_3$).

(iv) Alcohol (14) (4.3 g, 15.1 mmol) was dissolved in ammonium hydroxide (30 mL) and a solution of ammonia in 2-propanol (20 mL, 2.0M, 80 mmol). The solution was divided into two equal portions then heated at 75° C. in sealed tubes for 16 hours. The mixtures were combined using methanol then the solvents were removed in vacuo. The residue was azeotroped with diethyl ether (3×20 mL) to obtain (R)-2-amino-1-((S)-2,5-dihydrofuran-2-yl)ethanol which was used without further purification.

A solution of sodium carbonate (3.37 g, 31.8 mmol) in water (24 mL) was added whilst stirring to a suspension of (R)-2-amino-1-((S)-2,5-dihydrofuran-2-yl)ethanol (assumed to be 15.1 mmol) in 1,4-dioxane (30 mL). The mixture was cooled to 0° C. then benzylchloroformate (2.7 mL, 18.9 mmol) was added dropwise over 10 minutes. The mixture was stirred at 0° C. for 45 minutes then dichloromethane (100 mL) and water (150 mL) added. The organic phase was separated and the aqueous extracted with dichloromethane (2×50 mL). The organic layer was washed with brine (50 mL), then dried (Na$_2$SO$_4$), filtered and reduced in vacuo to leave a residue (5.2 g). Flash chromatography over silica, eluting with ethyl acetate:heptane mixtures 20:80 to 70:30 gave alcohol (18) (3.09 g, 78%). $[\alpha]_D^{16.5}$ −58.7° (c=5.88, CHCl$_3$).

Alternative preparation of Benzyl(R)-2-((S)-2,5-dihydrofuran-2-yl)-2-hydroxyethylcarbamate (18); Zinc and 'One-pot' procedure. A solution of ammonium chloride (600 mg, 11.2 mmol) in water (7.5 mL) was added to a solution of bromotosylate (47) (3.0 g, 8.26 mmol) in propan-2-ol (15 mL) under argon. Zinc dust (600 mg, 9.2 mmol) was then added in portions over 4 minutes and the mixture was stirred for 16 hours before filtering the suspension through celite in vacuo. The filter cake was washed with diethyl ether (60 mL). Hydrochloric acid (1M, 60 mL) was added to the filtrate then the organic phase separated. The aqueous layer was extracted with diethyl ether (60 mL) then the combined organic phase was washed with brine (60 mL), then dried (MgSO$_4$), filtered and reduced in vacuo. The residue was dissolved in ammonium hydroxide (18 mL) and a solution of ammonia in propan-2-ol (12 mL, 2.0M, 24 mmol), then divided into two equal portions and heated in sealed tubes at 75° C. for 16 hours. The mixtures were combined using methanol then the solvents were removed in vacuo. The residue was azeotroped with diethyl ether (3×10 mL) to obtain (R)-2-amino-1-((S)-2,5-dihydrofuran-2-yl)ethanol which was used without further purification.

A solution of sodium carbonate (1.84 g, 17.4 mmol) in water (16 mL) was added whilst stirring to a suspension of (R)-2-amino-1-((S)-2,5-dihydrofuran-2-yl)ethanol (assumed to be 8.26 mmol) in 1,4-dioxane (20 mL). The mixture was cooled to 0° C. then benzylchloroformate (1.77 mL, 12.4 mmol) was added dropwise over 5 minutes. The mixture was stirred at 0° C. for 55 minutes then dichloromethane (75 mL) and water (100 mL) added. The organic phase was separated and the aqueous extracted with dichloromethane (2×50 mL). The organic phase was washed with brine (50 mL), then dried (Na$_2$SO$_4$), filtered and reduced in vacuo to leave a residue (3.7 g). Flash chromatography over silica, eluting with ethyl acetate:heptane mixtures 20:80 to 70:30 gave alcohol (18) (1.26 g, 58%). $[\alpha]_D^{16}$ −62.0° (c=5.0, CHCl$_3$).

Preparation of (R)-2-(Benzyloxycarbonylamino)-1-((S)-2,5-dihydrofuran-2-yl)ethyl 4-methyl benzenesulfonate (32b). A solution of p-toluenesulfonyl chloride (368 mg, 2.03 mmol) in pyridine (1.5 mL) was added to alcohol (18) (333 mg, 1.27 mmol). The mixture was stirred at 14° C. for 16 hours and at 24° C. for 3.5 hours then diluted with tert-butyl methyl ether (35 mL). The organic layer was washed with water (15 mL), brine (15 mL), then dried (MgSO$_4$), filtered and reduced in vacuo to leave a pale yellow oil (0.712 g). Flash chromatography over silica, eluting with ethyl acetate heptane mixtures 15:85 to 30:70 gave tosylate (32b) (429 mg, 81%) as a white solid. TLC (R$_f$ 0.75, EtOAc:heptane 3:1), analytical HPLC single main peak, R$_t$=18.93 min., HPLC-MS 374.2, 418.2 [M+H]$^+$, 857.3 [2M+Na]$^+$; $[\alpha]_D^{18.5}$ −30.2° (c=1.326, CHCl$_3$); $\delta_H$ (500 MHz, CDCl$_3$) 2.39 (3H, s, aryl-CH$_3$), 3.29-3.37 and 3.53-3.62 (2H total, m, CH$_2$NH), 4.44-4.50 and 4.52-4.57 (2H total, m, OCH$_2$CH=CH), 4.59-4.65 (1H, m, OCHCH=CH), 4.87-4.92 (1H, m, CHOTs), 5.05 (2H, m, OCH$_2$Ph), 5.03 (1H, brs, NH), 5.69-5.73 and 5.94-5.98 (2H total, m, CH$_2$CH=CH), 7.28 (2H, d, J=8.10 Hz, aromatic CH$_3$CCH), 7.29-7.37 (5H, phenyl CH), 7.77 (2H, d, J=8.10 Hz, aromatic OSO$_2$CCH); $\delta_C$ (125 MHz, CDCl$_3$) 21.627 (aryl-CH$_3$), 41.119 (CH$_2$NHCbz), 66.856 (CH$_2$Ph), 75.987 (OCH$_2$CH=CH), 82.352 (CHOTs), 85.622 (OCHCH=CH), 124.792, 127.825, 128.027, 128.126, 128.504, 129.357 and 129.537 (OCH$_2$CH=CCH and aromatic CH), 133.674 (CHOSO$_2$C quaternary), 136.348 (Cbz quaternary), 144.941 (CH$_3$C quaternary), 156.273 (Cbz C=O).

Epoxidation Studies with (R)-2-(Benzyloxycarbonylamino)-1-((S)-2,5-dihydro furan-2-yl)ethyl 4-methylbenzenesulfonate (32b)

(a) 3-Chloroperbenzoic acid (97 mg, ≦77%, 0.43 mmol) was added to a stirred solution of alkene (32b) (36 mg, 0.086 mmol) in dichloromethane (1.5 mL). The mixture was stirred for 20 hours at ambient temperature then 3-chloroperbenzoic acid (97 mg, ≦77%, 0.43 mmol) was added and stirring continued for 1 day at 24° C. then diluted with dichloromethane (15 mL). The organic phase was washed with aqueous sodium hydroxide solution (5%, 10 mL), water (10 mL), then dried (Na$_2$SO$_4$), filtered and reduced in vacuo to leave a residue (0.038 mg). Flash chromatography over silica, eluting with ethyl acetate:heptane mixtures 10:90 to 50:50 gave (in order of elution) anti-(33b) (16 mg, 43%) as a colourless viscous oil and syn-epoxide (9 mg, 24%) as a white solid. Data for anti-(33b); TLC (R$_f$=0.50, EtOAc:heptane 1:1), analytical HPLC single main peak, R$_t$=17.999 min., HPLC-MS 434.1 [M+H]$^+$, 456.1 [M+Na]$^+$, 889.2 [2M+Na]$^+$; $[\alpha]_D^{17}$ +25.6° (c 2.54, CHCl$_3$); $\delta_H$ (500 MHz, CDCl$_3$) 2.41 (3H, s, aryl-CH$_3$), 3.31-3.38 and 3.60-3.66 (2H total, m, CH$_2$NH), 3.67 (1H, d, J=10.46 Hz, OCH$_2$CH), 3.75 and 3.81 (each 1H, d, J=2.50 and 2.75 Hz respectively, OCH$_2$CHCH), 3.94 (1H, d, J=10.57 Hz, OCH$_2$CH), 4.07 (1H, d, J=6.90 Hz, OCH-CHOTs), 4.60-4.64 (1H, m, CHOTs), 4.97-5.01 (1H brt, NH), 5.08 (2H, brs, CH$_2$Ph), 7.29-7.37 (7H, aromatic CH$_3$CCH and phenyl CH), 7.78 (2H, d, J=8.18 Hz, aromatic OSO$_2$CCH); $\delta_C$ (125 MHz, CDCl$_3$) 21.665 (aryl-CH$_3$), 42.054 (CH$_2$NHCbz), 56.175 and 57.048 (OCH$_2$CHCH), 67.031 (CH$_2$Ph), 67.672 (OCH$_2$CH), 76.732 (OCHCHOTs), 79.388 (CHOTs), 127.776, 128.108, 128.222, 128.544 and 130.043 (aromatic CH), 133.249 (CHOSO$_2$C quaternary), 136.192 (Cbz quaternary), 145.487 (CH$_3$C quaternary), 156.224 (Cbz C=O). Data for syn-epoxide; TLC (R$_f$=0.42, EtOAc:heptane 1:1), analytical HPLC single main peak, R$_t$=18.009 min., HPLC-MS 434.1 [M+H]$^+$, 889.2 [2M+Na]$^+$; $\delta_H$ (500 MHz, CDCl$_3$) 2.40 (3H, s, aryl-CH$_3$), 3.40-3.47 and 3.58-3.63 (2H total, m, CH$_2$NH), 3.62 and 3.72 (each 1H, d and dd respectively, J=2.84 and 3.01, 0.60 Hz respectively, OCH$_2$CHCH), 3.67 (1H, d, J=10.68 Hz, OCH$_2$CH), 3.92 (1H, d, J=7.07 Hz, OCHCHOTs), 3.97 (1H, d, J=10.67 Hz, OCH$_2$CH), 4.65-4.70 (1H, m, CHOTs), 5.00-5.04 (1H brt, NH), 5.05 (2H, brs, CH$_2$Ph), 7.29-7.37 (7H, aromatic CH$_3$CCH and phenyl CH), 7.83 (2H, d, J=8.11 Hz, aromatic OSO$_2$CCH); $\delta_C$ (125 MHz, CDCl$_3$) 21.664 (aryl-CH$_3$), 41.958 (CH$_2$NHCbz), 55.948 and 56.425 (OCH$_2$CHCH), 66.823 (CH$_2$Ph), 68.008 (OCH$_2$CH), 76.498 (OCHCHOTs), 78.395 (CHOTs), 127.986, 128.072, 128.110, 128.493 and 129.928 (aromatic CH), 133.189 (CHOSO$_2$C quaternary), 136.383 (Cbz quaternary), 145.177 (CH$_3$C quaternary), 156.202 (Cbz C=O).

(b) To a solution of alkene (32b) (262 mg, 0.63 mmol) in acetonitrile (4 mL) and aqueous Na$_2$.EDTA (4 mL, 0.4 mmol solution) at 0° C. was added 1,1,1-trifluoroacetone (0.67 mL, 7.54 mmol) via a pre-cooled syringe. To this solution was added in portions a mixture of sodium bicarbonate (0.44 g, 5.28 mmol) and OXONE® (1.20 g, 1.95 mmol) over a period of 55 minutes. The mixture was stirred for 2.5 hours then diluted with water (25 mL) and the product extracted into dichloromethane (2×25 mL). The combined organic layers were washed with brine (12.5 mL) then dried (Na$_2$SO$_4$), filtered and reduced in vacuo to leave a residue (310 mg). Flash chromatography over silica, eluting with ethyl acetate: heptane mixtures 15:85 to 50:50 gave anti-(33b) as a viscous white oil (216 mg, 79%).

(c) To a solution of alkene (32b) (4.74 g, 11.35 mmol) in acetonitrile (260 mL) and aqueous Na$_2$.EDTA (80 mL, 0.4 mM solution) at 0° C. was added 1,1,1-trifluoroacetone (12.19 mL, 136.24 mmol) via a pre-cooled syringe. To this solution was added in portions a mixture of sodium bicarbonate (8.01 g, 95.37 mmol) and OXONE® (21.64 g, 35.19 mmol) over a period of 1 hour. The mixture was stirred for 1 hour then diluted with water (500 mL) and the product extracted into dichloromethane (3×200 mL). The combined organic layers were washed with aqueous sodium hydrogen sulphite solution (5%, 200 mL) then dried (Na$_2$SO$_4$), filtered and reduced in vacuo to leave a residue that was recrystallised from ethanol (20 mL) to give anti-(33b) as a white solid (0.68 g, 14%). $[\alpha]_D^{16}$+30.1° (c=7.14, CHCl$_3$).

(d) To a solution of alkene (32b) (1.48 g, 3.54 mmol) in acetonitrile (85 mL) and aqueous Na$_2$.EDTA (25 mL, 0.4 mM solution) at 0° C. was added 1,1,1-trifluoroacetone (3.81 mL, 42.54 mmol) via a pre-cooled syringe. To this solution was added in portions a mixture of sodium bicarbonate (2.5 g, 29.8 mmol) and OXONE® (6.76 g, 10.99 mmol) over a period of 1 hour. The mixture was stirred for 1 hour then diluted with water (150 mL) and the product extracted into dichloromethane (3×60 mL). The combined organic layers were washed with aqueous sodium hydrogen sulphite solution (5%, 60 mL) then dried (Na$_2$SO$_4$), filtered and reduced in vacuo to leave a residue that was recrystallised from propan-2-ol (15 mL) to give anti-(33b) as an off-white solid (0.54 g, 35%). The mother liquor was concentrated in vacuo to leave a residue (0.98 g). Flash chromatography over silica, eluting with ethyl acetate:heptane 1:2 gave anti-(33b) (0.555 g, 36%).

(e) Acetonitrile (0.2 mL, 3.8 mmol), then hydrogen peroxide (30% in water, 0.271 mL), then sodium bicarbonate (50 mg) were added to a stirred solution of alkene (32b) (100 mg, 0.24 mmol) in methanol (3 mL). The mixture was stirred for 5 days before adding acetonitrile (0.2 mL, 3.8 mmol), then hydrogen peroxide (30% in water, 0.271 mL), then sodium bicarbonate (50 mg). The mixture was stirred for an additional 2 days before adding acetonitrile (0.2 mL, 3.8 mmol), then hydrogen peroxide (30% in water, 0.271 mL), then sodium bicarbonate (50 mg). The mixture was stirred for 1 day then reduced in vacuo, then the residue partitioned between water (10 mL) and ethyl acetate (2×15 mL). The organic phase was dried (MgSO$_4$), filtered and reduced in vacuo. $^1$H nmr analysis of the residue indicated an approximate ratio of 10:1:3 of anti-(33b): syn-epoxide: starting material alkene (32b) respectively to be present.

Preparation of (3aS,6aR)-(9H-Fluoren-9-yl)methyl 3-oxotetrahydro-2H-furo[3,2-b]pyrrole-4(5H)-carboxylate (2c)

(i) Preparation (3R,3aR,6R,6aS)— tert-Butyl 3-hydroxy-6-(tosyloxy)tetrahydro-2H-furo[3,2-b]pyrrole-4(5H)-carboxylate (35b). Ethanol (1.5 mL) was added dropwise to a mixture of 10% palladium on charcoal (20 mg) and anti-(33b) (100 mg, 0.25 mmol) under an atmosphere of argon. The argon was replaced by hydrogen then the suspension was stirred for 4.5 hours before filtering the mixture through celite in vacuo. The filter cake was washed with ethanol (10 mL) then the solvents removed in vacuo from the filtrate. The residue was azeotroped with toluene (2×3 mL) to obtain (3R,3aR,6R,6aS)-3-hydroxyhexahydro-2H-furo[3,2-b]pyrrol-6-yl 4-methylbenzenesulfonate which was used without further purification.

A solution of sodium carbonate (56 mg, 0.275 mmol) in water (0.75 mL) was added whilst stirring to a solution of (3R,3aR,6R,6aS)-3-hydroxyhexahydro-2H-furo[3,2-b]pyrrol-6-yl 4-methylbenzenesulfonate in 1,4-dioxane (0.75 mL). A solution of di-tert-butyl dicarbonate (60 mg, 0.275 mmol) in 1,4-dioxane (0.5 mL) was added dropwise over 5 minutes then the mixture stirred for 1 hour before adding an additional aliquot of di-tert-butyl dicarbonate (40 mg, 0.184 mmol) in 1,4-dioxane (0.25 mL) dropwise over 1 minute. The mixture was stirred for 70 minutes then water (5 mL) was added and the product extracted into dichloromethane (3×5 mL). The organic layer was washed with brine (5 mL), then dried (Na$_2$SO$_4$), filtered and reduced in vacuo to leave a residue (132 mg). Flash chromatography over silica, eluting with ethyl acetate:heptane mixtures 15:85 to 45:55 gave bicyclic alcohol (35b) (58.9 mg, 60%) as a white solid. TLC (R$_f$=0.30, EtOAc:heptane 1:1), analytical HPLC single main peak, R$_f$=16.54 min., HPLC-MS 344.1 [M+2H-$^t$Bu]$^+$, 821.3 [2M+Na]$^+$; $[\alpha]_D^{18.5}$–30.3° (c=6.10, CHCl$_3$); $\delta_H$ (500 MHz, CDCl$_3$) mixture of rotamers major:minor 2:1; 1.44 (6H, brs, (CH$_3$)$_3$C, major), 1.46 (3H, brs, (CH$_3$)$_3$C, minor), 1.98 (0.33H, d, J=4.00 Hz, OH minor), 2.44 (3H, s, aryl-CH$_3$), 2.69 (0.66H, d, J=2.88 Hz, OH major), 3.08-3.15 (0.33H, m, BocNCH$_2$ minor), 3.26-3.32 (0.66H, m, BocNCH$_2$ major), 3.75-3.87 (2H, m, 1×OCH$_2$CHOH and 1×BocNCH$_2$), 3.94-4.02 (1H, m, OCH$_2$CHOH), 4.07 (1H, brs, BocNCH), 4.35 (0.33H, brs, OCH$_2$CHOH minor), 4.41 (0.66H, brs, OCH$_2$CHOH major), 4.52 (0.66H, t, J=4.75 Hz, TsOCHCH major), 4.65 (0.33H, t, J=3.95 Hz, TsOCHCH minor), 4.72-4.78 (1H, m, TsOCHCH), 7.34 (2H, brd, J=7.82 Hz, aromatic CH$_3$CCH), 7.82 (2H, brd, J=8.01 Hz, aromatic OSO$_2$CCH); $\delta_C$ (125 MHz, CDCl$_3$) 21.681 (aryl-CH$_3$), 28.294/28.386 ((CH$_3$)$_3$C), 46.810/48.177 (BocNCH$_2$), 68.153/68.484 (BocNCH), 75.484/75.697 (OCH$_2$CHOH), 76.228/76.980 (OCH$_2$CHOH), 76.269/76.585 (TsOCHCH), 79.391/80.233 (TsOCHCH), 81.079/81.139 ((CH$_3$)$_3$C quarternary), 127.973, 129.911, 129.966 and 130.125 (aromatic CH), 133.144 (CHOSO$_2$C quaternary), 145.247 (CH$_3$C quaternary), 153.161/154.244 (Boc C=O).

(ii) Preparation of (3R,3aR,6aR)-tert-Butyl 3-hydroxytetrahydro-2H-furo[3,2-b]pyrrole-4(5H)-carboxylate (2f). A solution of Super-Hydride® (12.5 mL, 1M in tetrahydrofuran, 12.5 mmol) was added dropwise over 2 minutes to a stirred solution of bicyclic alcohol (35b) (1 g, 2.51 mmol) in tetrahydrofuran (20 mL) under an atmosphere of argon. The mixture was heated for 1 hour at 40° C. then an additional aliquot of Super-Hydride® (12.5 mL, 1M in tetrahydrofuran, 12.5 mmol) was added. The mixture was heated at 40° C. for 1 hour then cooled to 0° C. Water (100 mL) was cautiously added and the product extracted into dichloromethane (3×100 mL). The organic phase was washed with a mixture of brine and water (1:1, 500 mL), then dried (Na$_2$SO$_4$), filtered and reduced in vacuo to leave an oil. Flash chromatography over silica, eluting with ethyl acetate:heptane mixtures 0:100 to 50:50 gave bicyclic alcohol (2f) (416 mg, 72%) as a viscous colourless oil. TLC (R$_f$=0.25, EtOAc:heptane 2:1); HPLC-MS 174.1 [M+2H-$^t$Bu]$^+$, 252.1 [M+Na]$^+$, 481.3 [2M+Na]$^+$; $[\alpha]_D^{13}$–72.8° (c=4.26, CHCl$_3$); $\delta_H$ (500 MHz, CDCl$_3$) mixture of rotamers major:minor 5:3; 1.45 and 1.49 (9H total, each s, (CH$_3$)$_3$C), 1.83-1.93 and 1.98-2.05 (2H total, m, BocNCH$_2$CH$_2$), 2.08 (0.38H, d, J=4.00 Hz, OH minor), 2.85 (0.62H, d, J=2.37 Hz, OH major), 3.18-3.28, 3.53-3.58 and 3.67-3.73 (3H total, m, BocNCH$_2$CH$_2$ and BocNCH), 3.92-3.96 (0.38H, m, OCH$_2$CHOH minor), 3.99-4.10 (1.62H, m, OCH$_2$CHOH), 4.34 (0.38H, brs, OCH$_2$CHOH minor), 4.37 (0.68H, brs, OCH$_2$CHOH major), 4.71 (0.62H, brt, J=4.78 Hz, OCHCHN major), 4.75 (0.38H, brt, J=4.78 Hz, OCHCHN minor); $\delta_C$ (125 MHz, CDCl$_3$) 28.433/28.533 ((CH$_3$)$_3$C), 31.273/31.557 (BocNCH$_2$CH$_2$), 44.866/45.260

(BocNCH$_2$), 69.777/70.392 (BocNCH), 74.116/74.375 (OCH$_2$CHOH), 77.092/77.708 (OCH$_2$CHOH), 80.113/80.154 ((CH$_3$)$_3$C quarternary), 81.803/82.634 (OCHCHN), 153.690/154.798 (Boc C=O).

(iv) Preparation of (3R,3aR,6aR)-(9H-fluoren-9-yl)methyl 3-hydroxytetrahydro-2H-furo[3,2-b]pyrrole-4(5H)-carboxylate (2b). Alcohol (2f) (558 mg, 2.43 mmol) was dissolved in 4M HCl in dioxane (14.06 mL) and left to stand at ambient temperature for 1 h. The solvent was removed in vacuo and the residue azeotroped from toluene (3×20 mL) to give hydrochloride salt of (3R,3aR,6aR)-hexahydro-2H-furo[3,2-b]pyrrol-3-ol (2g) used directly in the following step.

(v) Preparation of (3R,3aR,6aR)-(9H-fluoren-9-yl)methyl 3-hydroxytetrahydro-2H-furo[3,2-b]pyrrole-4(5H)-carboxylate (2b). A solution of sodium carbonate (0.54 g, 5.11 mmol) in water (4 mL) was added whilst stirring to a solution of the HCl salt of aminoalcohol (2g) in 1,4-dioxane (10 mL). The solution was cooled to 0° C. then a solution of 9-fluorenylmethoxycarbonyl chloride (0.66 g, 2.56 mmol) in 1,4-dioxane (10 mL) was added dropwise over 30 minutes. The mixture stirred for 2 h then water (50 mL) was added and the product extracted into dichloromethane (2×50 mL). The organic layer was washed with brine (50 mL), then dried (Na$_2$SO$_4$), filtered and reduced in vacuo to leave an oily residue. Flash chromatography over silica, eluting with ethyl acetate:heptane mixtures 15:85 to 50:50 gave alcohol (2b) as a white solid (0.324 g, 0.93 mmol). Data for alcohol (2b). TLC (R$_f$=0.15, EtOAc:heptane 1:1), analytical HPLC single main peak, R$_t$=15.81 min., HPLC-MS 352.1 [M+H]$^+$, 374.1 [M+Na]$^+$, 725.1 [2M+Na]$^+$.

(vi) Oxidation of alcohol (2b) to ketone (2c). Dess-Martin periodinane (1.52 g, 3.6 mmol) was added to a stirred solution of alcohol (2b) (660 mg of approximately 90% purity, 1.7 mmol) in dichloromethane (25 mL) under an atmosphere of nitrogen. The mixture was stirred for 1.25 hours then diluted with dichloromethane (50 mL). The organic phase was washed with a mixture of saturated aqueous sodium bicarbonate and 0.25M sodium thiosulphate solution (1:1), then saturated aqueous sodium bicarbonate then brine, then dried (Na$_2$SO$_4$), filtered and reduced in vacuo. Flash chromatography over silica, eluting with ethyl acetate:heptane mixtures 10:90 to 40:60 gave ketone (2c) (611 mg, quantitative) as a white solid. TLC (R$_f$=0.30, EtOAc:heptane 1:1), analytical HPLC broad main peak, R$_t$=15.311-17.960 min., HPLC-MS 350.2 [M+H]$^+$, 372.2 [M+Na]$^+$, 390.2 [M+H$_2$O+Na]$^+$, 721.3 [2M+Na]$^+$; [α]$_D^{16}$-133.2° (c=1.84, CHCl$_3$). Analysis by $^1$H and $^{13}$C NMR showed the presence of rotamers around the amide bond. $^1$H NMR δ$_H$ (400 MHz, CDCl$_3$) 1.61-1.97/2.10-2.15 (2H, m, NCH$_2$CH$_2$), 3.32-3.45 (1H, m, NCH$_2$CH$_2$), 3.66-3.75/3.85-3.95 (2×0.5H, m, NCH$_2$CH$_2$), 3.95/4.10 (2H, m, COCH$_{2A}$+COCH$_{2B}$), 4.15-4.30 (3H, m, Fmoc H-9+Fmoc CH$_2$), 4.40-4.60/4.80-4.92 (2H, complex, FmocNCH+ OCHCH$_2$), 7.20-7.30 (2H, Fmoc H-2 and H-7), 7.31-7.42 (2H, Fmoc H-3 and H-6), 7.50-7.57/7.60-7.66 (2H, Fmoc H-1 and H-8), 7.68-7.76 (2H, Fmoc H-4 and H-5); δ$_C$ (100 MHz, CDCl$_3$) 31.76/32.28 (NCH$_2$CH$_2$), 45.59/45.95 (NCH$_2$CH$_2$), 47.64 (Fmoc C-9), 62.26/62.77 (C$_α$), 68.03/68.65 (Fmoc CH$_2$), 71.28 (COCH$_2$), 82.17/83.11 (C$_β$), 120.38 (Fmoc C-4 and C-5), 125.41/125.59/125.88 (Fmoc C-1 and C-8), 127.45/127.49 (Fmoc C-2 and C-7), 128.13 (Fmoc C-3 and C-6), 141.73 (Fmoc C-4' and C-5'), 144.16/144.37/144.88 (Fmoc C-1' and C-8'), 155.33 (OCON), 209.32 (COCH$_2$).

Preparation of 4-(4-cyclobutylpiperazin-1-yl)benzoic Acid (64)

(i) Methyl 4-(piperazin-1-yl)benzoate (CAS163210-97-7, 500 mg, 2.27 mmol) was dissolved in THF (10 mL) and water (0.2 mL) with stirring. Cyclobutanone (0.238 g, 3.4 mmol) was added followed by acetic acid (0.5 mL) and sodium cyanoborohydride (0.211 g, 3.4 mmol). The mixture was refluxed for 6 h, cooled and reduced in vacuo. The residue was dissolved in 1N HCl (3 mL) and water (12 mL) then washed with ethyl acetate (2×10 mL). The aqueous layer was adjusted to pH 10 with potassium carbonate and extracted with ethyl acetate (3×10 mL). The combined organics were dried (MgSO$_4$), filtered and reduced in vacuo to give crude methyl ester (0.56 g).

(ii) Methyl ester (0.51 g, assume 1.85 mmol) was suspended in 10% NaOH (3 mL) and water (3 mL) added. The mixture was heated at 80° C. for 2 h, then cooled to 0° C. The mixture was acidified to pH 2 with 6N HCl, then cooled for 2 h at –5° C. A tan solid was filtered and washed thoroughly with hexane and dried in vacuo to give acid (64) (yield 0.25 g). HPLC-MS 261 [M+H]$^+$.

Preparation of 4-(1-cyclopropylpiperidin-4-yl)benzoic Acid (66)

(i) Methyl 4-(piperidin-4-yl)benzoate (CAS 281235-04-9, 0.5 g, 2.27 mmol) was dissolved in a mixture of THF (10 mL) and MeOH (10 mL). Acetic acid (1.38 g, 22.7 mmol) and [(1-ethoxycyclopropyl)oxy]trimethylsilane (0.8 g, 4.6 mmol) were added followed by sodium cyanoborohydride (0.433 g, 6.9 mmol). The mixture was stirred for 7 h then reduced in vacuo. The residue was dissolved in 1N HCl (3 mL) and water (12 mL) then washed with ethyl acetate (2×10 mL). The aqueous layer was adjusted to pH 10 with potassium carbonate and extracted with ethyl acetate (3×10 mL). The combined organics were washed with brine then dried (MgSO$_4$), filtered and reduced in vacuo to give crude methyl ester (0.35 g). The crude ester was purified over silica gel eluting with hexane:ethyl acetate (85:15 v/v).

(ii) Methyl ester (0.20 g, assume 0.77 mmol) was suspended in 10% NaOH (2.5 mL) and water (2.5 mL) added. The mixture was heated at 80° C. for 2 h, then cooled to 0° C. The mixture was acidified to pH 2 with 6N HCl, then cooled for 2 h at –5° C. A solid was filtered and washed thoroughly with hexane and dried in vacuo to give acid (66) (yield 0.04 g).

Preparation of 4-(1-cyclobutylpiperidin-4-yl)benzoic Acid (67)

(i) Methyl 4-(piperidin-4-yl)benzoate (CAS 281235-04-9, 0.25 g, 1.13 mmol) was dissolved in a mixture of THF (6 mL) and water (0.1 mL). Acetic acid (0.25 mL) and cyclobutanone (0.119 g, 1.7 mmol) were added followed by sodium cyanoborohydride (0.15 g, 2.4 mmol). The mixture was refluxed for 5 h then cooled and reduced in vacuo. The residue was dissolved in 1N HCl (4 mL) and water (15 mL) then washed with ethyl acetate (2×10 mL). The aqueous layer was adjusted to pH 10 with potassium carbonate and extracted with ethyl acetate (3×10 mL). The combined organics were washed with brine then dried (MgSO$_4$), filtered and reduced in vacuo to give crude methyl ester (0.23 g).

(ii) Methyl ester (0.23 g, assume 0.84 mmol) was suspended in 10% NaOH (2.5 mL) and water (2.5 mL) added. The mixture was heated at 80° C. for 2 h, then cooled to 0° C. The mixture was acidified to pH 2 with 6N HCl, then cooled for 2 h at −5° C. A solid was filtered and washed thoroughly with hexane and dried in vacuo to give acid (67) (yield 0.1 g).

Solid Phase Chemistry

Fmoc-ketone building block (2c) was utilised in a solid phase synthesis of example inhibitors (3-10) of general formula I and closely related prior art EXAMPLES 1 and 2. The methods used were directly analogous to those described in detail in WO02057270, utilising the 4-{[(Hydrazinocarbonyl)amino]methyl}cyclohexane carboxylic acid trifluoroacetate based linker, solid phase lanterns (ex Mimotopes), standard Fmoc chemistries and acidolytic cleavage followed by semi-preparative HPLC purification (see WO02057270 pg 124-127 for full generic details). Alternative EXAMPLES of the invention can readily be prepared by the general methods detailed in WO02057270 through use of the appropriately derivatised 4-(4-alkylpiperazin-1-yl)benzoic acid or 4-(1-alkylpiperidin-4-yl)benzoic acid building block (general synthetic details for preparation are given in WO0158886) 4-(4-propylpiperazin-1-yl)benzoic acid (CAS 354813-21-1), 4-(4-isopropylpiperazin-1-yl)benzoic acid (CAS 354813-24-4), 4-(4-(2-methoxyethyl)piperazin-1-yl)benzoic acid (CAS 354813-30-2), 4-(4-cyclopropylpiperazin-1-yl)benzoic acid (CAS 883743-83-7), 4-(1-propylpiperidin-4-yl)benzoic acid (CAS 354813-33-5), 4-(1-isopropylpiperidin-4-yl)benzoic acid (CAS 354813-42-6), 4-(1-(2-methoxyethyl)piperidin-4-yl)benzoic acid (CAS 354813-38-0). Additional novel preferred carboxylic acids are prepared by simple adaptation of the general methods detailed in WO01058886.

Example 1

4-(4-methylpiperazin-1-yl)-N—((S)-4-methyl-1-oxo-1-((3aS,6aR)-3-oxo dihydro-2H-furo[3,2-b]pyrrol-4(5H,6H,6aH)-yl)pentan-2-yl)benzamide Prior art compound 42 (Quibell, M. et. al. *Bioorg. Med. Chem.*, 13, 609-625, 2005); Prior art compound 45a (Quibell, M. et. al. *Bioorg. Med. Chem.*, 12, 5689-5710, 2004);

(EXAMPLE 1)

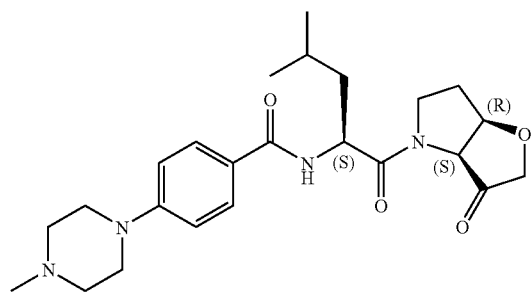

HPLC-MS $R_t$=2.85 min, 443.2 [M+H]$^+$, 461.2 [M+H+18]$^+$, 907.3 [2M+Na]$^+$.

Example 2

Closely Related Analogue for Comparison 4-(4-ethylpiperazin-1-yl)-N—((S)-4-methyl-1-oxo-1-((3aS,6aR)-3-oxo dihydro-2H-furo[3,2-b]pyrrol-4(5H,6H,6aH)-yl)pentan-2-yl)benzamide (EXAMPLE 2)

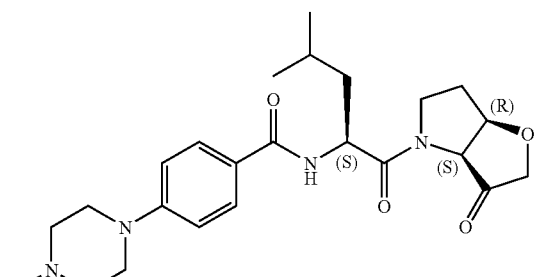

HPLC-MS $R_t$=3.06 min, 457.2 [M+H]$^+$, 475.3 [M+H+18]$^+$, 935.5 [2M+Na]$^+$.

Example 3

N—((S)-4-methyl-1-oxo-1-((3aS,6aR)-3-oxo-dihydro-2H-furo[3,2-b]pyrrol-4(5H,6H,6aH)-yl)pentan-2-yl)-4-(4-propylpiperazin-1-yl)benzamide (EXAMPLE 3)

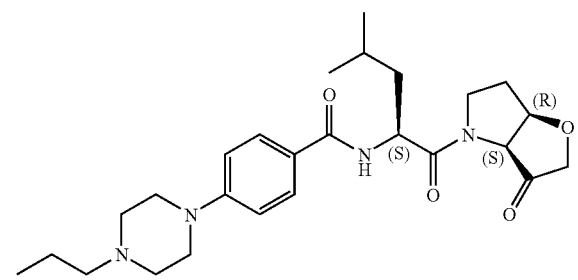

HPLC-MS $R_t$=3.23 min, 471.3 [M+H]$^+$, 489.3 [M+H+18]$^+$, 963.5 [2M+Na]$^+$.

Example 4

4-(4-isopropylpiperazin-1-yl)-N—((S)-4-methyl-1-oxo-1-((3aS,6aR)-3-oxo dihydro-2H-furo[3,2-b]pyrrol-4(5H,6H,6aH)-yl)pentan-2-yl)benzamide (EXAMPLE 4)

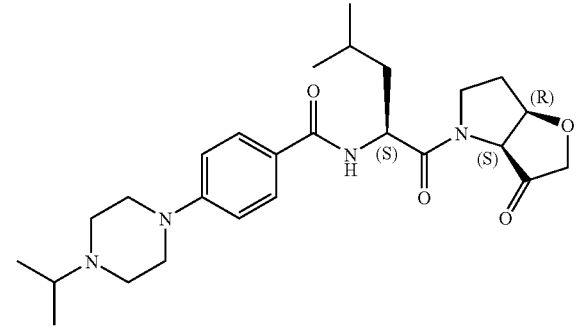

HPLC-MS $R_t$=3.14 min, 471.3 [M+H]$^+$, 489.3 [M+H+18]$^+$, 963.5 [2M+Na]$^+$.

Example 5

4-(4-(2-methoxyethyl)piperazin-1-yl)-N—((S)-4-methyl-1-oxo-1-((3aS,6aR)-3-oxo dihydro-2H-furo[3,2-b]pyrrol-4(5H,6H,6aH)-yl)pentan-2-yl)benzamide (EXAMPLE 5)

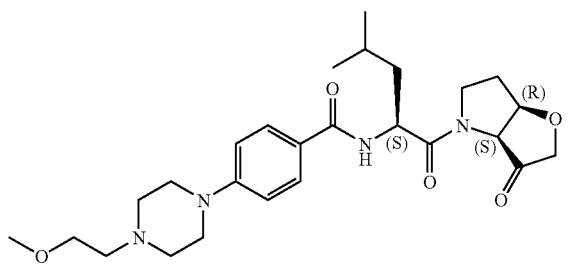

HPLC-MS $R_t$=3.05 min, 487.2 [M+H]$^+$, 505.2 [M+H+18]$^+$, 995.3 [2M+Na]$^+$.

Example 6

4-(4-cyclopropylpiperazin-1-yl)-N—((S)-4-methyl-1-oxo-1-((3aS,6aR)-3-oxo dihydro-2H-furo[3,2-b]pyrrol-4(5H,6H,6aH)-yl)pentan-2-yl)benzamide (EXAMPLE 6)

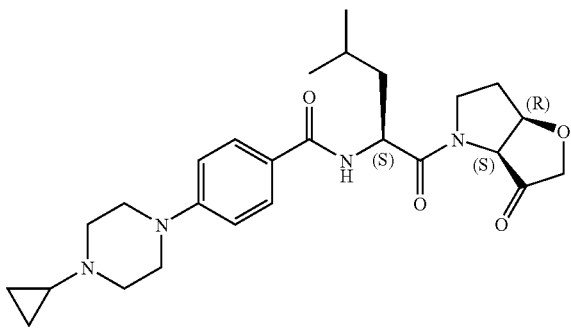

HPLC-MS $R_t$=3.11 min, 469.2 [M+H]$^+$, 487.3 [M+H+18]$^+$, 959.5 [2M+Na]$^+$.

Example 7

4-(1-cyclobutylpiperazin-4-yl)-N—((S)-4-methyl-1-oxo-1-((3aS,6aR)-3-oxo dihydro-2H-furo[3,2-b]pyrrol-4(5H,6H,6aH)-yl)pentan-2-yl)benzamide (EXAMPLE 7)

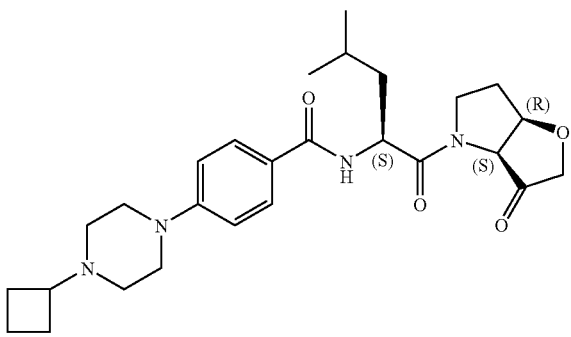

HPLC-MS $R_t$=3.27 min, 483.3 [M+H]$^+$, 501.3 [M+H+18]$^+$, 987.5 [2M+Na]$^+$.

Example 8

4-(1-(2-methoxyethyl)piperidin-4-yl)-N—((S)-4-methyl-1-oxo-1-((3aS,6aR)-3-oxodihydro-2H-furo[3,2-b]pyrrol-4(5H,6H,6aH)-yl)pentan-2-yl)benzamide (EXAMPLE 8)

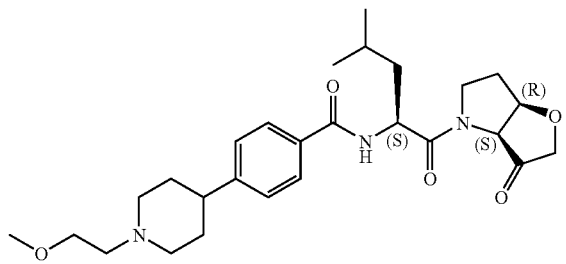

HPLC-MS $R_t$=3.24 min, 486.2 [M+H]$^+$, 504.2 [M+H+18]$^+$, 993.3 [2M+Na]$^+$.

Example 9

4-(1-cyclopropylpiperidin-4-yl)-N—((S)-4-methyl-1-oxo-1-((3aS,6aR)-3-oxodihydro-2H-furo[3,2-b]pyrrol-4(5H,6H,6aH)-yl)pentan-2-yl)benzamide (EXAMPLE 9)

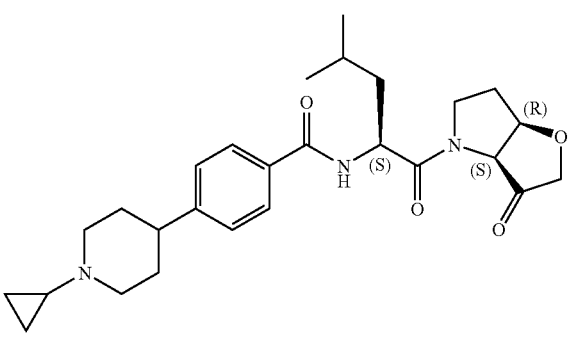

HPLC-MS $R_t$=3.27 min, 468.3 [M+H]$^+$, 486.3 [M+H+18]$^+$, 957.5 [2M+Na]$^+$.

Example 10

4-(1-cyclobutylpiperidin-4-yl)-N—((S)-4-methyl-1-oxo-1-((3aS,6aR)-3-oxodihydro-2H-furo[3,2-b]pyrrol-4(5H,6H,6aH)-yl)pentan-2-yl)benzamide (EXAMPLE 10)

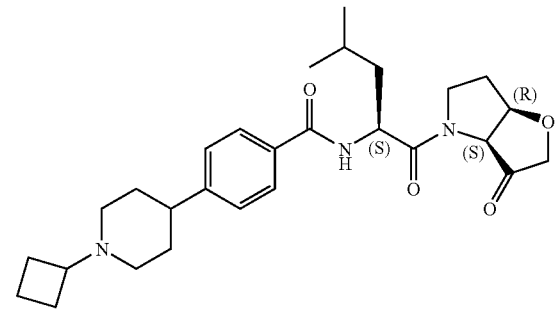

HPLC-MS $R_t$=3.47 min, 482.3 [M+H]$^+$, 500.3 [M+H+18]$^+$, 963.5 [2M+H]$^+$.

Solution Phase Syntheses.

Alternatively, examples of the invention may be prepared by traditional solution phase organic chemistry techniques.

Alternative Preparation of N—((S)-4-methyl-1-oxo-1-((3aS,6aR)-3-oxo-dihydro-2H-furo[3,2-b]pyrrol-4(5H,6H,6aH)-yl)pentan-2-yl)-4-(4-propylpiperazin-1-yl)benzamide Example 3

(i) Preparation of tert-Butyl(S)-1-((3R,3aR,6aR)-3-hydroxydihydro-2H-furo[3,2-b]pyrrol-4(5H,6H,6aH)-yl)-4-methyl-1-oxopentan-2-ylcarbamate  4-Methylmorpholine (0.721 mL, 6.61 mmol) was added to a stirred solution of (3R,3aR,6aR)-hexahydro-2H-furo[3,2-b]pyrrol-3-ol hydrochloride (2g) (6.61 mmol) in dimethylformamide (3 mL) under argon. The mixture was stirred for 2 minutes then a solution of (S)-tert-butyl 1-fluoro-4-methyl-1-oxopentan-2-ylcarbamate (1.54 g, 6.61 mmol) in dimethylformamide (1.5 mL) was added. The flask containing the (S)-tert-butyl 1-fluoro-4-methyl-1-oxopentan-2-ylcarbamate solution was rinsed into the reaction mixture with dimethylformamide (1 mL then 0.5 mL). The mixture was stirred for 1.5 hours then the solvents removed in vacuo. Flash chromatography over silica, eluting with ethyl acetate:pentane mixtures 0:100 to 100:0 gave tert-butyl(S)-1-((3R,3aR,6aR)-3-hydroxydihydro-2H-furo[3,2-b]pyrrol-4(5H,6H,6aH)-yl)-4-methyl-1-oxopentan-2-ylcarbamate as a pale yellow solid (1.35 g, 60%). TLC ($R_f$=0.20, methanol:dichloromethane 1:19), analytical HPLC main peak, $R_t$=12.20 min., HPLC-MS 287.2 [M+2H-$^t$Bu]$^+$, 343.2 [M+H]$^+$, 365.2 [M+Na]$^+$, 707.4 [2M+Na]$^+$; $[\alpha]_D^{23}$ –43.7° (c=7.78, CHCl$_3$); $\delta_H$ (500 MHz, CDCl$_3$) mixture of rotamers major:minor 11:9; 0.91-0.98 (6H, m, CH(CH$_3$)$_2$), 1.42 (9H, s, OC(CH$_3$)$_3$), 1.32-1.82 (3.55H, m, CH$_2$CH(CH$_3$)$_2$ and NCH$_2$CH$_2$CH major), 1.93-2.04 (0.45H, m, NCH$_2$CH$_2$CH minor), 2.04 (0.55H, dd, J=13.86 and 6.17 Hz, NCH$_2$CH$_2$CH major), 2.16 (0.45H, dd, J=13.79 and 6.45 Hz, NCH$_2$CH$_2$CH minor), 3.15 (0.45H, brs, OH minor), 3.22-3.28 (0.55H, m, NCH$_2$CH$_2$CH major), 3.41-3.47 (0.45H, m, NCH$_2$CH$_2$CH minor), 3.51 (0.55H, dd, J=8.63 and 7.08 Hz, OCH$_2$CHOH major), 3.64 (0.45H, dd, J=9.65 and 5.27 Hz, OCH$_2$CHOH minor), 3.88 (0.55H, dd, J=11.90 and 8.38 Hz, NCH$_2$CH$_2$CH major), 3.90 (0.45H, brt, J=9.03 Hz, NCH$_2$CH$_2$CH minor), 4.02 (0.45H, dd, J=9.65 and 5.67 Hz, OCH$_2$CHOH minor), 4.15-4.28 (2.55H, m, OCH$_2$CHOHCH and 1×OCH$_2$CHOH major), 4.45-4.50 (0.45H, m, CHCH$_2$CH(CH$_3$)$_2$ minor), 4.64-4.70 (0.55H, m, CHCH$_2$CH(CH$_3$)$_2$ major), 4.70 (0.45H, brt, J=5.71 Hz, NCH$_2$CH$_2$CH minor), 4.75 (0.55H, brt, J=5.21 Hz, NCH$_2$CH$_2$CH major), 5.17 (0.45H, d, J=9.14 Hz, NH minor), 5.22 (0.55H, d, J=10.09 Hz, NH major), 5.45 (0.55H, d, J=4.66 Hz, OH major); $\delta_C$ (125 MHz, CDCl$_3$) 21.83/21.89/23.27/23.32/24.53 and 24.68 (CH(CH$_3$)$_2$), 28.23/28.32 (OC(CH$_3$)$_3$), 30.13/31.66 (NCH$_2$CH$_2$CH), 42.00/42.46/44.02 and 45.53 (NCH$_2$CH$_2$CH and CH$_2$CH(CH$_3$)$_2$), 50.11/50.36 (CHCH$_2$CH(CH$_3$)$_2$), 71.13/71.29 (NCH$_2$CH$_2$CHCH), 73.02/74.03 (OCH$_2$CHOH), 77.35/79.55 (CHOH), 79.74/80.80 (OC(CH$_3$)$_3$), 80.95/83.39 (NCH$_2$CH$_2$CH), 155.63/156.57 (Boc C=O), 171.97/172.49 (CH$_2$NC=O).

(ii) Preparation of N—((S)-1-((3R,3aR,6aR)-3-Hydroxydihydro-2H-furo[3,2-b]pyrrol-4(5H, 6H,6aH)-yl)-4-methyl-1-oxopentan-2-yl)-4-(4-propylpiperazin-1-yl)benzamide A solution of HCl in 1,4-dioxane (4.0M, 22 mL, 88 mmol) was added to tert-butyl(S)-1-((3R,3aR,6aR)-3-hydroxydihydro-2H-furo[3,2-b]pyrrol-4(5H,6H,6aH)-yl)-4-methyl-1-oxopentan-2-ylcarbamate (1.335 g, 3.90 mmol). The solution was stirred for 2.5 hours then the solvents removed in vacuo and the residue azeotroped with toluene (3×30 mL) to leave (S)-2-amino-1-((3R,3aR,6aR)-3-hydroxydihydro-2H-furo[3,2-b]pyrrol-4(5H,6H,6aH)-yl)-4-methylpentan-1-one hydrochloride as an off-white solid which was used without further purification. TLC ($R_f$=0.0, EtOAc:heptane 3:1), analytical HPLC main peak, $R_t$=3.54 min., HPLC-MS 243.2 [M+H]$^+$, 507.3 [2M+Na]$^+$.

4-Methylmorpholine (0.90 mL, 8.19 mmol) was added to a suspension of 2-(1H-benzotriazole-1-yl)-1,1,3,3-tetramethyluronium hexafluorophosphate (HBTU, 1.55 g, 4.10 mmol), 1-hydroxybenzotriazole monohydrate (627 mg, 4.10 mmol) and 4-(4-propylpiperazin-1-yl)benzoic acid (85% wt., 1.25 g, 4.29 mmol) in dimethylformamide (6 mL). The suspension was shaken for 5 minutes then added to a stirred solution of (S)-2-amino-1-((3R,3aR,6aR)-3-hydroxydihydro-2H-furo[3,2-b]pyrrol-4(5H,6H,6aH)-yl)-4-methylpentan-1-one hydrochloride (prepared as above, assume 3.90 mmol) in dimethylformamide (10 mL). Residual material was washed into the reaction flask using dimethylformamide (2×2 mL). After 2.5 hours the majority of solvents were removed in vacuo. The residue was dissolved in dichloromethane (100 mL) and washed with saturated sodium hydrogen carbonate solution (75 mL). The aqueous phase was extracted with dichloromethane (2×50 mL) then the combined organic layers washed with brine (50 mL), then dried (Na$_2$SO$_4$), filtered and reduced in vacuo. Flash chromatography over silica, eluting with heptane:ethyl acetate mixtures 100:0:0 to 100 then methanol:dichloromethane mixtures 1:99 to 5:95 gave N—((S)-1-((3R,3aR,6aR)-3-hydroxydihydro-2H-furo[3,2-b]pyrrol-4(5H,6H, 6aH)-yl)-4-methyl-1-oxopentan-2-yl)-4-(4-propylpiperazin-1-yl)benzamide as an off-white solid (1.67 g, 91%). TLC ($R_f$=0.15-0.25 double spot, MeOH:CH$_2$Cl$_2$ 1:19), analytical HPLC main peak, $R_t$=10.11 min., HPLC-MS 473.3 [M+H]$^+$, 967.6 [2M+Na]$^+$; $[\alpha]_D^{19.5}$+2.99° (c=6.7, CHCl$_3$); $\delta_H$ (500 MHz, CDCl$_3$) mixture of rotamers major:minor 2:1; 0.93 (3H, t, J=7.39 Hz, CH$_2$CH$_3$), 0.92-1.02 (6H, m, CH(CH$_3$)$_2$), 1.47-1.86 (5.67H, m, CH$_2$CH(CH$_3$)$_2$ CH$_2$CH$_3$ and NCH$_2$CH$_2$CH major), 1.97-2.06 (0.33H, m, NCH$_2$CH$_2$CH minor), 2.05 (0.67H, dd, J=13.83 and 6.17 Hz, NCH$_2$CH$_2$CH major), 2.18 (0.33H, dd, J=13.80 and 6.33 Hz, NCH$_2$CH$_2$CH minor), 2.35-2.34 (2H, m, NCH$_2$CH$_2$CH$_3$), 2.57-2.61 (4H, m, CH$_2$CH$_2$NCH$_2$CH$_3$), 3.22-3.30 (0.67H, m, NCH$_2$CH$_2$CH major), 3.29-3.34 (4H, m, CH$_2$CH$_2$NCH$_2$CH$_3$), 3.47-3.54 (0.33H, m, NCH$_2$CH$_2$CH minor), 3.52 (0.67H, dd, J=9.46 and 7.87 Hz, OCH$_2$CHOH major), 3.66 (0.33H, dd, J=9.57 and 5.27 Hz, OCH$_2$CHOH minor), 3.89 (0.67H, dd, J=11.84 and 8.48 Hz, NCH$_2$CH$_2$CH major), 4.04 (0.33H, brt, J=8.91 Hz, NCH$_2$CH$_2$CH minor), 4.04 (0.33H, dd, J=9.55 and 5.15 Hz, OCH$_2$CHOH minor), 4.17 (0.67H, dd, J=9.50 and 6.92 Hz, OCH$_2$CHOH major), 4.23-4.30 (2H, m, OCH$_2$CHOHCH), 4.70 (0.33H, brt, J=4.76 Hz, NCH$_2$CH$_2$CH minor), 4.76 (0.67H, brt, J=5.24 Hz, NCH$_2$CH$_2$CH major), 5.00-5.05 (0.33H, m, CHCH$_2$C(CH$_3$)$_3$ minor), 5.23-5.28 (0.67H, m, CHCH$_2$C(CH$_3$)$_3$ major), 5.94 (0.67H, brd, J=4.68 Hz, OH major), 6.69 (0.67H, d, J=9.82 Hz, NH major), 6.58 (0.33H, d, J=8.32 Hz, NH minor), 6.86 (2H, d, J=8.98 Hz, aromatic CH), 7.69-7.72 (2H, m, aromatic CH); $\delta_C$ (125 MHz, CDCl$_3$) 11.88 (CH$_2$CH$_3$), 19.90/19.92 (CH$_2$CH$_3$), 22.00/22.07/23.32/23.37/24.70 and 24.86 (CH(CH$_3$)$_2$), 30.06/31.67 (NCH$_2$CH$_2$CH), 42.17/42.57/44.07 and 45.68 (NCH$_2$CH$_2$CH and CH$_2$CH(CH$_3$)$_2$), 47.56/47.69 (NCH$_2$CH$_2$NCH$_2$CH$_3$), 49.17/49.21 (CHCH$_2$CH(CH$_3$)$_2$), 52.85/52.89 (NCH$_2$CH$_2$NCH$_2$CH$_3$), 60.38/60.57 (NCH$_2$CH$_2$CH$_3$), 71.27/71.43 (NCH$_2$CH$_2$CHCH), 73.08/74.11 (OCH$_2$CHOH), 77.35/79.71 (CHOH), 81.00/83.41 (NCH$_2$CH$_2$CH), 113.97/114.12/128.51 and 128.77 (aromatic CH), 122.27/123.32 (aromatic quaternary), 153.47/153.74 (aromatic quaternary), 166.68/167.61 (NHC=O), 171.63/172.32 ($CH_2NC=O$).

(iii) Oxidation to Example 3 Dess-Martin periodinane (1.83 g, 4.30 mmol) was added to a stirred solution of N—((S)-1-((3R,3aR,6aR)-3-hydroxydihydro-2H-furo[3,2-b]pyrrol-4(5H,6H, 6aH)-yl)-4-methyl-1-oxopentan-2-yl)-4-(4-propylpiperazin-1-yl)benzamide (250 mg, 0.546 mmol) in dichloromethane (45 mL) under an atmosphere of argon. The mixture was stirred for 18.5 hours then diluted with dichloromethane (200 mL). The organic phase was washed with aqueous sodium hydroxide solution (1M, 70 mL) then the aqueous extracted with dichloromethane (75 mL). The organic layer was washed with aqueous sodium hydroxide solution (1M, 70 mL) then brine (70 mL), then dried ($Na_2SO_4$), filtered and reduced in vacuo to give Example 3 as a pale yellow solid (0.831 g, 82%). TLC ($R_f$=0.30, MeOH:$CH_2Cl_2$ 1:9), analytical HPLC main peak, $R_t$=9.80 min., HPLC-MS 471.3 $[M+H]^+$, 489.3 $[M+H_2O+H]^+$, 963.6 $[2M+Na]^+$; $[\alpha]_D^{21}$ −92.8° (c=3.29, $CHCl_3$); $\delta_H$ (500 MHz, $CDCl_3$)- hydrate not assigned here 0.91 (3H, d, J=6.58 Hz, $CH(CH_3)_2$), 0.93 (3H, t, J=7.32 Hz, $CH_2CH_3$), 1.00 (3H, d, J=6.47 Hz, $CH(CH_3)_2$), 1.52-1.78 (5H, m, $CH_2CH(CH_3)_2$ and $CH_2CH_3$), 2.06-2.15 (1H, m, $NCH_2CH_2CH$), 2.29 (1H, dd, J=13.69 and 6.09 Hz, $NCH_2CH_2CH$), 2.40-2.45 (2H, m, $NCH_2CH_2CH_3$), 2.66 (4H, brt, J=4.80 Hz, $CH_2NCH_2CH_2CH_3$), 3.35 (4H, brt, J=5.01 Hz, $CH_2CH_2NCH_2CH_2CH_3$), 3.55-3.62 (1H, m, $NCH_2CH_2CH$), 3.98 (1H, d, J=17.03 Hz, $OCH_2C=O$), 4.14 (1H, d, J=16.96 Hz, $OCH_2C=O$), 4.17 (1H, brt, J=8.89 Hz, $NCH_2CH_2CH$), 4.66 (1H, d, J=5.16 Hz, $NCH_2CH_2CHCH$), 4.89 (1H, t, J=4.35 Hz, $NCH_2CH_2CHCH$), 5.01-5.06 (1H, m, $CHCH_2CH(CH_3)_2$), 6.79 (1H, d, J=8.45 Hz, NH), 6.87 (2H, brd, J=8.97 Hz, aromatic CH), 7.70 (2H, brd, J=8.94 Hz, aromatic CH); $\delta_C$ (125 MHz, $CDCl_3$) 11.91 ($CH_2CH_3$), 19.95 ($CH_2CH_3$), 22.12/23.28 and 24.77 ($CH(CH_3)_2$), 32.48 ($NCH_2CH_2CH$), 42.67 ($CH_2CH(CH_3)_2$), 45.60 ($NCH_2CH_2CHCH$), 47.72 ($NCH_2CH_2NCH_2CH_3$), 49.52 ($CHCH_2CH(CH_3)_2$), 52.89 ($NCH_2CH_2NCH_2CH_3$), 60.58 ($NCH_2CH_2CH_3$), 62.15 ($NCH_2CH_2CHCH$), 71.02 ($OCH_2C=O$), 80.78 ($NCH_2CH_2CHCH$), 114.06/114.09/128.51 and 128.59 (aromatic CH), 123.26 (aromatic quaternary), 153.49 (aromatic quaternary), 166.78 (NHC=O), 172.41 ($CH_2NC=O$), 208.43 (ketone C=O).

Formation of EXAMPLE Hydrochloride Salt.

EXAMPLE ketone (free base) (1 mmol) was dissolved in acetonitrile (16.7 mL) and standardised 0.1N HCl (1.5 eq, 15.0 mL) was added. The mixture was frozen and lyophilised to leave the EXAMPLE hydrochloride salt as a solid.

Example A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

In Vitro Cathepsin Ki Inhibition Measurements

Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.). The equilibrium inhibition constants ($K_i^{ss}$) for each compound were measured under steady-state conditions monitoring enzyme activity as a function of inhibitor concentration. The values were calculated on the assumption of pure competitive behaviour (Cornish-Bowden, A. *Fundamentals of enzyme kinetics* Portland Press; 1995, 93-128). Human recombinant cathepsin K (0.25 nM final; B. Turk, Josef, Stefan Institute, Ljubljana, Slovenia), was routinely assayed in 100 mM sodium acetate; pH 5.5 containing 1 mM EDTA, 10 mM L-cysteine and 1.8 μM Z-Leu-Arg-AMC ($[S]=K_M$).

Measurement of the Apparent Macroscopic Binding (Michaelis) Constants ($K_M^{app}$) for Substrates The apparent macroscopic binding constant ($K_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics* Portland Press; 1995, 93-128).

$$v_i = \frac{V_{max}^{app} \cdot [S_o]}{[S_o] + K_M^{app}} \quad (1)$$

In Equation 1 '$v_i$' is the observed initial rate, '$V_{max}^{app}$' is the observed maximum activity at saturating substrate concentration, '$K_M^{app}$' is the apparent macroscopic binding (Michaelis) constant for the substrate, '$[S_o]$' is the initial substrate concentration.

Measurement of the Inhibition Constants

The apparent inhibition constant ($K_i$) for each compound was determined on the basis that inhibition was reversible and occurred by a pure-competitive mechanism. The $K_i$ values were calculated, from the dependence of enzyme activity as a function of inhibitor concentration, by direct regression analysis (Prism v 3.02) using Equation 2 (Cornish-Bowden, A., 1995).

$$v_i = \frac{V_{max}^{app} \cdot [S]}{[S] + \{K_M^{app} \cdot ([I]/K_i)\}} \quad (2)$$

In Equation 2 '$v_i$' is the observed residual activity, '$V_{max}^{app}$' is the observed maximum activity (i.e. in the absence of inhibitor), '$K_M^{app}$' is the apparent macroscopic binding (Michaelis) constant for the substrate, '[S]' is the initial substrate concentration, '$K_i$' is the apparent dissociation constant and '[I]' is the inhibitor concentration.

In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.*, 7, 102-105, 1982; Morrison, J. F. *Biochim. Biophys. Acta*, 185, 269-286, 1969; Stone, S. R. and Hofsteenge, J. *Biochemistry*, 25, 4622-4628, 1986).

$$v_i = \cfrac{F\left\{\begin{array}{c} E_o - I_o - K_i^{app} + \\ \sqrt{(E_o - I_o - K_i^{app})^2 + 4 \cdot K_i^{app} \cdot E_o} \end{array}\right\}}{2} \quad (3)$$

$$K_i^{app} = K_i(1 + [S_o]/K_M^{app}) \quad (4)$$

In Equation 3 '$v_i$' is the observed residual activity, 'F' is the difference between the maximum activity (i.e. in the absence of inhibitor) and minimum enzyme activity, '$E_o$' is the total enzyme concentration, '$K_i^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_i$' is the inhibition constant, '$[S_o]$' is the initial substrate concentration and '$K_M^{app}$' is the apparent macroscopic binding (Michaelis) constant for the substrate (Morrison, 1982).

The Second-Order Rate of Reaction of Inhibitor with Enzyme

Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., *TIBS*, 102-105, 1982; Tian, W. X. and Tsou, C. L., *Biochemistry*, 21, 1028-1032, 1982; Morrison, J. F. and Walsh, C. T., from Meister (Ed.), *Advances in Enzymol.*, 61, 201-301, 1988; Tsou, C. L., from Meister (Ed.), *Advances in Enzymol.*, 61, 381-436, 1988). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot t)}]}{k_{obs}} + D \quad (5)$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$). To correct for substrate kinetics, Eq. 6 was used, where '$[S_o]$' is the initial substrate concentration and "$K_M^{app}$" is the apparent macroscopic binding (Michaelis) constant for the substrate.

$$k_{inact} = \frac{k_{obs}(1 + [S_o]/K_M^{app})}{[I]} \quad (6)$$

Compounds of the invention were tested by the above described assays and observed to exhibit cathepsin K inhibitory activity with an in vitro Ki inhibitory constant of less than or equal to 100 nM.

Liver Microsomal Incubations

Human and rat liver microsomes were purchased from BD Gentest (Woburn, Mass., USA) and β-nicotinamide adenine dinucleotide 2'-phosphate reduced tetrasodium salt (NADPH) was purchased from Sigma-Aldrich (Poole, Dorset, UK). All liver microsome incubations were carried out in 50 mM potassium phosphate buffer at pH 7.4, with a final microsomal protein concentration of 0.5 mg/mL. Compounds were taken from 5 mM DMSO stock solutions and diluted in incubation buffer to give a final concentration of 25 µM, with a final DMSO concentration of 0.5% v/v. In brief, compounds were added to the incubation buffer along with the liver microsomes and incubated at 37° C. for 10 minutes. The reaction was then initiated by the addition of NADPH, previously dissolved in incubation buffer, to give a final concentration of 1 mM and re-incubated at 37° C. Aliquots were removed at 2 and 60 minutes and quenched with an equal volume of cold acetonitrile. After mixing vigorously, the precipitated protein matter was removed by filtration (Multiscreen Solvinert filter plates, Millipore, Bedford, Mass., USA) and the filtrate analysed by reverse phase HPLC with mass spectrometric detection, using single ion monitoring of the [M+H]$^+$ species. Metabolic turnover was determined by comparison of peak areas from the ion chromatograms of the parent compound at 2 and 60 minutes and expressed as percent remaining at 1 hour.

Plasma Incubations

Human and rat plasma were purchased from Innovative Research Inc. (Southfield. MI, USA). Compounds were taken from 5 mM DMSO stock solutions and added to plasma, which had previously been incubated at 37° C., to give a final concentration of 25 µM and re-incubated. Aliquots were removed at 2 and 60 minutes and quenched with an equal volume of cold acetonitrile. After mixing vigorously, the precipitated protein matter was removed by filtration (Multiscreen Solvinert filter plates, Millipore, Bedford, Mass., USA) and the filtrate analysed by reverse phase HPLC with mass spectrometric detection, using single ion monitoring of the [M+H]$^+$ species. Metabolic turnover was determined by comparison of peak areas from the ion chromatograms of the parent compound at 2 and 60 minutes and expressed as percent remaining at 1 hour.

LogD Determinations

LogD$_{(PBS)}$ determinations were performed in 96 well microtitre plates using a miniaturised "shake-flask" method. In brief, compounds were taken from 10 mM DMSO stock solutions and added to wells containing equal volumes of phosphate buffered saline (10 mM; pH 7.4) (PBS) and 1-octanol (Sigma-Aldrich, Poole, Dorset, UK) to give a final concentration of 50 µM. The plates were then capped and mixed vigorously for 1 hour on a microtitre plate shaker, after which they were left to stand, allowing the PBS and octanol phases to separate. The PBS layer was analysed by reverse phase HPLC with mass spectrometric detection, using single ion monitoring of the [M+H]$^+$ species. LogD$_{(PBS)}$ was determined by comparison of the peak area from the ion chromatogram of the compound in the PBS phase with that of a 50 µM standard of the same compound dissolved in acetonitrile/water (50:50) and calculated using the following formula:

$$\text{Log}D = \text{Log}\left[\frac{AUCstd - AUCpbs}{AUCpbs}\right]$$

Where AUCstd and AUCpbs are the peak areas from the standard and test ion chromatograms respectively. LogD$_{(PBS)}$ determinations were also made using PBS at pH6.9 and 5.5 by adjusting the pH of the buffer prior to the start of the assay, with 0.1 M HCL.

Human Osteoclast Resorption Assay

Bone resorption was studied using a model where human osteoclast precursor cells were cultured on bovine bone slices for 9 days and allowed to differentiate into bone-resorbing osteoclasts. The formed mature osteoclasts were then allowed to resorb bone. The assay was performed by Pharmatest Services Ltd, Itainen Pitkakatu 4C, Turku, Finland. After the culture period, bone collagen degradation products were quantified from the culture medium as an index of bone resorption. Inhibitor compounds were added into the cell cultures after the differentiation period and their effects on the resorbing activity of mature osteoclasts were determined. The studies included a baseline group without added compounds and a positive control group where a potent cathepsin K inhibitor E-64 was added.

Human peripheral blood monocytes were suspended to culture medium and allowed to attach to bovine bone slices. The bone slices were transferred into 96-well tissue culture plates containing culture medium with appropriate amounts of important growth factors favouring osteoclast differentiation, including M-CSF, RANK-ligand and TGF-β. The cells were incubated in a $CO_2$ incubator in humidified atmosphere of 95% air and 5% carbon dioxide at 37° C. At day 7 when osteoclast differentiation was complete, the culture medium was replaced with culture medium containing conditions favouring osteoclast activity. The cell culture was continued for an additional 2 days, during which the formed mature osteoclasts were allowed to resorb bone in the presence of vehicle, control inhibitor (E64) or test compounds. At the end of the culture, bone collagen degradation products released into the culture medium were determined using a commercially available ELISA method (CrossLaps® for culture, Nordic Bioscience, Herlev, Denmark) as an index of bone resorption (see Bagger, Y. Z. et al, J. Bone. Miner. Res. 14 (suppl. 1), S370).

In this assay, selected EXAMPLES of the invention exhibited more than 50% inhibition of bone resorption at a concentration of 100 nM.

Rat Osteoclast Resorption Assay

Bone resorption was studied using a model where mature osteoclasts derived from rat bone were cultured on bovine bone slices for 3 days and allowed to resorb bone in the presence of inhibitor, positive control (E-64) or vehicle. More specifically, tibia, femori and humeri were removed from 1 day old rat pups. The endosteal surfaces of the bones were scraped with a scapelto release osteoclasts into the culture medium and the osteoclasts were allowed to attach to bovine bone slices. After the culture period, bone collagen degradation products were quantified from the culture medium as an index of bone resorption. The assay was performed by Pharmatest Services Ltd, Itäinen Pitkakatu 4C, Turku, Finland.

In this assay, selected EXAMPLES of the invention exhibited more than 50% inhibition of bone resorption at a concentration of 500 nM.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Comparison of biological properties for preferred compounds (3-10) prior art compounds (1) and non-preferred close analogue (2).

| EXAMPLE | In vitro Ki (nM) vs Cath K | Cell-based % Inh. @ 1 μM Human | Cell-based % Inh. @ 1 μM Rat | Human Plasma Stability % rem. @ 1 h | HLM % rem. @ 1 h | LogD pH 7.4 |
|---|---|---|---|---|---|---|
| | 87.4 | Lit. 60 | | 75 | 70 | 1.36 |

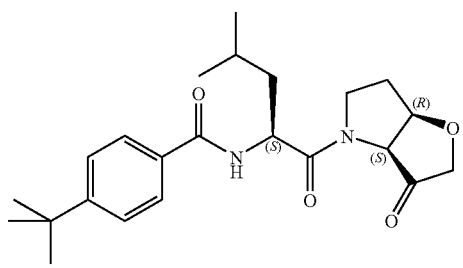

Prior art compound 23 (Quibell, M. et. al. Bioorg. Med. Chem., 13, 609-625, 2005);
Prior art compound 10 (Quibell, M. et. al. Bioorg. Med. Chem., 12, 5689-5710, 2004);

TABLE 1-continued

Comparison of biological properties for preferred compounds (3-10) prior art compounds (1) and non-preferred close analogue (2).

| EXAMPLE | In vitro Ki (nM) vs Cath K | Cell-based % Inh. @ 1 µM Human | Cell-based % Inh. @ 1 µM Rat | Human Plasma Stability % rem. @ 1 h | HLM % rem. @ 1 h | LogD pH 7.4 |
|---|---|---|---|---|---|---|
| 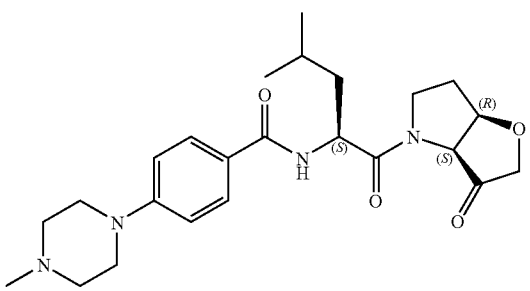 Prior art compound 42 (Quibell, M. et. al. Bioorg. Med. Chem., 13, 609-625, 2005); Prior art compound 45a (Quibell, M. et. al. Bioorg. Med. Chem., 12, 5689-5710, 2004); | 8.7 | 55 | 43 | 95 | 95 | Lit. 0.04* 0.56** *UV method **Ion-count method |
| 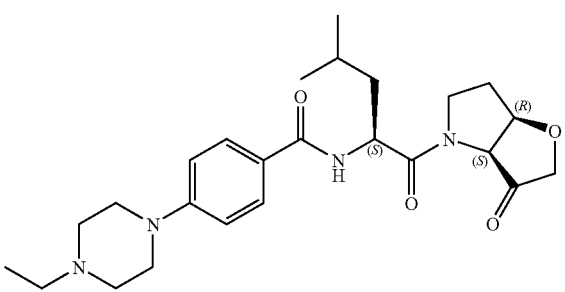 (EXAMPLE 2) | 15 | 58 | 40 | 93 | 88 | 0.74 |
| 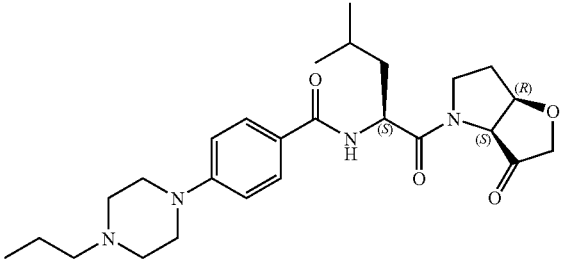 (EXAMPLE 3) | 18 | 73 | 65 | 89 | 83 | 1.66 |
| 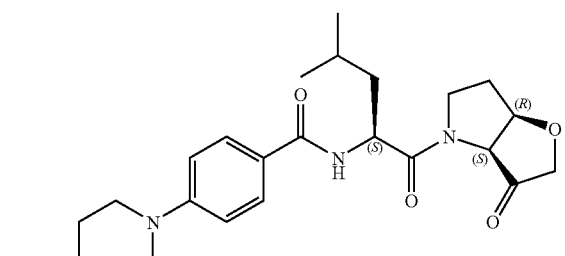 (EXAMPLE 4) | 19 | 74 | 25 | 91 | 88 | 1.21 |

TABLE 1-continued
Comparison of biological properties for preferred compounds (3-10) prior art
compounds (1) and non-preferred close analogue (2).
| EXAMPLE | In vitro Ki (nM) vs Cath K | Cell-based % Inh. @ 1 μM Human | Cell-based % Inh. @ 1 μM Rat | Human Plasma Stability % rem. @ 1 h | HLM % rem. @ 1 h | LogD pH 7.4 |
|---|---|---|---|---|---|---|
| (EXAMPLE 5) 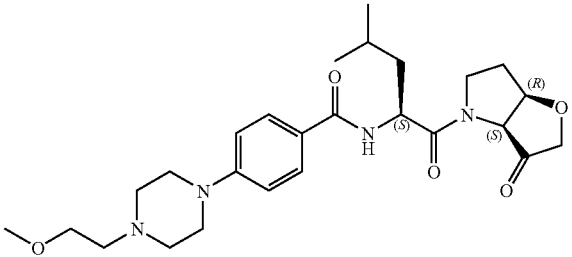 | 29 | 57 | 65 | 98 | 90 | 0.9 |
| (EXAMPLE 6) 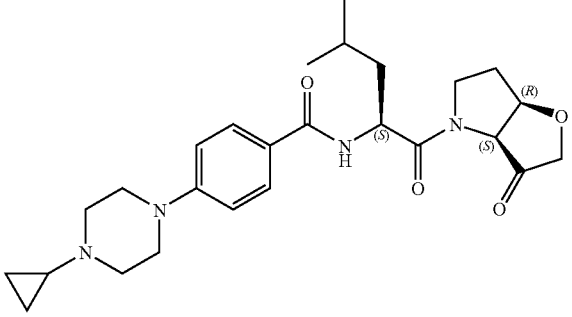 | 4 | 74 | 22 | 93 | 83 | 1.88 |
| (EXAMPLE 7) 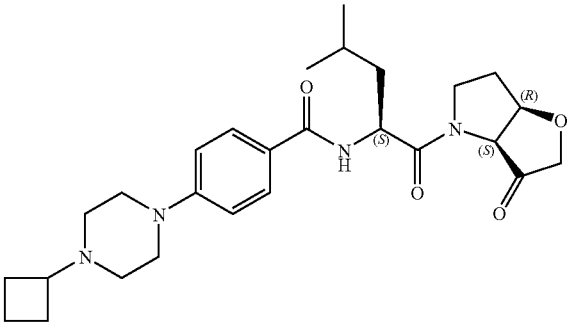 | 3 | 82 | 40 | 92 | 81 | 1.88 |
| (EXAMPLE 8) 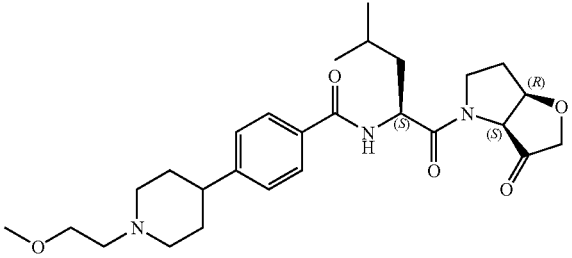 | 36 | 23 | 52 | 98 | 88 | 0.61 |

TABLE 1-continued

Comparison of biological properties for preferred compounds (3-10) prior art compounds (1) and non-preferred close analogue (2).

| EXAMPLE | In vitro Ki (nM) vs Cath K | Cell-based % Inh. @ 1 μM Human | Cell-based % Inh. @ 1 μM Rat | Human Plasma Stability % rem. @ 1 h | HLM % rem. @ 1 h | LogD pH 7.4 |
|---|---|---|---|---|---|---|
| 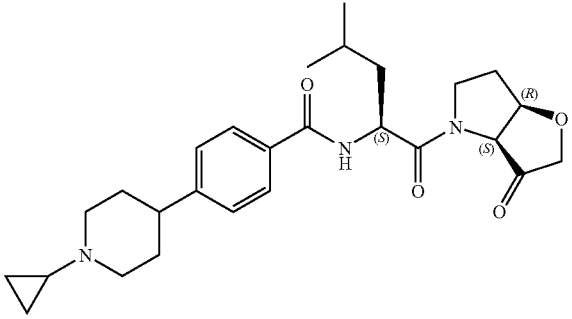 (EXAMPLE 9) | 8 | | | 93 | 82 | 1.99 |
| 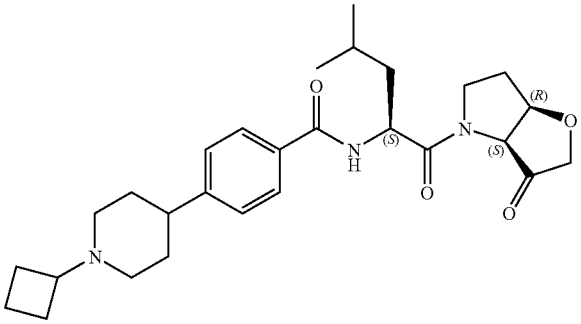 (EXAMPLE 10) | 5 | | | 90 | 83 | 0.95 |

TABLE 2

Prior art WO-A-02057270 in vitro Ki against recombinant human cathepsin K.

| Example No (WO-A-02057270) | Ki (nM) vs Human Cathepsin K |
|---|---|
| 1 | >20000 |
| 2 | >50000 |
| 3 | >4000 |
| 4 | >100000 |
| 5 | >100000 |
| 6 | >20000 |
| 7 | >15000 |
| 8 | 390 |
| 9 | 90 |
| 10 | 87 |
| 11 | 1300 |
| 12 | 170 |
| 13 | 560 |
| 14 | 300 |
| 15 | 60 |
| 16 | 110 |
| 17 | 235 |
| 18 | 130 |
| 19 | 530 |
| 20 | 390 |
| 21 | 210 |
| 22 | 450 |
| 23 | >3000 |
| 24 | >2000 |
| 25 | 620 |
| 26 | >8000 |
| 27 | >20000 |
| 28 | >2500 |
| 29 | >17000 |
| 30 | >100000 |
| 31 | >1500 |
| 32 | >16000 |
| 33 | >36000 |
| 34 | >67000 |
| 35 | >32000 |
| 36 | 570 |
| 37 | >3500 |
| 38 | >4000 |
| 39 | >7500 |
| 40 | >3500 |
| 41 | >45000 |
| 42 | >1500 |
| 43 | >25000 |
| 44 | >40000 |

TABLE 2-continued

Prior art WO-A-02057270 in vitro Ki against recombinant human cathepsin K.

| Example No (WO-A-02057270) | Ki (nM) vs Human Cathepsin K |
|---|---|
| 45 | >8500 |
| 46 | >20000 |
| 47 | 830 |
| 48 | >6500 |
| 49 | >6000 |
| 50 | >10000 |
| 51 | >1500 |
| 52 | >25000 |
| 53 | 200 |
| 54 | >2000 |
| 55 | >2000 |
| 56 | >4000 |
| 57 | 390 |
| 58 | >23000 |
| 59 | >2000 |
| 60 | >20000 |
| 61 | >16000 |
| 62 | >10000 |
| 63 | >250 |
| 64 | >8000 |
| 65 | 100 |
| 66 | >2500 |
| 67 | >2000 |
| 68 | >2500 |
| 69 | >15000 |
| 70 | >2500 |
| 71 | >20000 |
| 72 | >20000 |
| 73 | >35000 |
| 74 | >40000 |
| 75 | >50000 |
| 76 | >10000 |
| 77 | >100000 |
| 78 | >2000 |
| 79 | >200 |
| 80 | >150 |
| 81 | >50000 |
| 82 | >50000 |

Selected compounds of the present invention are significantly more potent than those specifically detailed in prior art WO-A-02057270 when assayed in vitro against recombinant human cathepsin K (compare tables 1 and 2).

The invention claimed is:

1. A compound of formula (I), or a pharmaceutically acceptable salt, hydrate, ketal derivative or hemiketal derivative thereof,

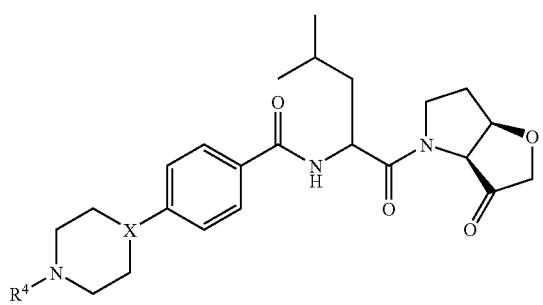

(I)

wherein:

X is CH or N; and $R^4$ is $C_{3-8}$ alkyl that is unsubstituted or substituted; or $C_{3-8}$ cycloalkyl that is unsubstituted or substituted.

2. A compound according to claim 1 wherein said compound is of formula Ia

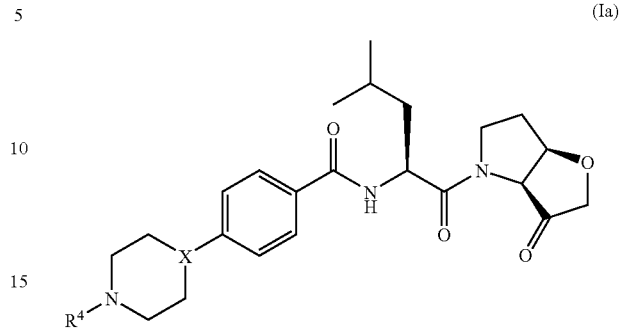

(Ia)

wherein X and $R^4$ are as defined in claim 1.

3. A compound according to claim 1 wherein X is CH.

4. A compound according to claim 1 wherein X is N.

5. A compound according to claim 1 wherein $R^4$ is an unsubstituted $C_{3-6}$ cycloalkyl group.

6. A compound according to claim 1 wherein $R^4$ is a $C_{3-8}$ alkyl group that is unsubstituted or substituted by one or more $C_{1-6}$ alkoxy groups.

7. A compound according to claim 1 wherein $R^4$ is selected from n-propyl, isopropyl, cyclopropyl, n-butyl, s-butyl, i-butyl, tert-butyl, cyclobutyl and 2-methoxyethyl.

8. A compound according to claim 7 wherein $R^4$ is selected from n-propyl, isopropyl, cyclopropyl, cyclobutyl and 2-methoxyethyl.

9. A compound according to claim 1 which is selected from the group consisting of:

N—((S)-4-methyl-1-oxo-1-((3aS,6aR)-3-oxo-dihydro-2H-furo[3,2-b]pyrrol-4(5H,6H,6aH)-yl)pentan-2-yl)-4-(4-propylpiperazin-1-yl)benzamide;

N—((S)-4-methyl-1-oxo-1-((3aS,6aR)-3-oxo-dihydro-2H-furo[3,2-b]pyrrol-4(5H,6H,6aH)-yl)pentan-2-yl)-4-(1-propylpiperidin-4-yl)benzamide;

4-(4-isopropylpiperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

4-(1-isopropylpiperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

4-(4-(2-methoxyethyl)piperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

4-(1-(2-methoxyethyl)piperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

4-(4-cyclopropylpiperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

4-(1-cyclopropylpiperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide;

4-(4-cyclobutylpiperazin-1-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide; and 4-(1-cyclobutylpiperidin-4-yl)-N—((S)-4-methyl-1-oxo-1-((3aS,6aR)-3-oxo-dihydro-2H-furo[3,2-b]pyrrol-4(5H,6H,6aH)-yl)pentan-2-yl)benzamide.

10. A pharmaceutical or veterinary composition comprising a compound according to claim 1 and a pharmaceutically acceptable or veterinarily acceptable diluent, excipient and/or carrier.

11. A process for preparing a pharmaceutical or veterinary composition, said process comprising admixing a compound according to claim 1 with a pharmaceutically acceptable or veterinarily acceptable diluent, excipient and/or carrier.

12. A compound according to claim 1 which is selected from the following:
- N—((S)-4-methyl-1-oxo-1-((3aS,6aR)-3-oxo-dihydro-2H-furo[3,2-b]pyrrol-4(5H,6H,6aH)-yl)pentan-2-yl)-4-(4-propylpiperazin-1-yl)benzamide;
- 4-(4-isopropylpiperazin-1-yl)-N—((S)-4-methyl-1-oxo-1-((3aS,6aR)-3-oxo dihydro-2H-furo[3,2-b]pyrrol-4 (5H, 6H, 6aH)-yl)pentan-2-yl)benzamide;
- 4-(4-(2-methoxyethyl)piperazin-1-yl)-N—((S)-4-methyl-1-oxo-1-((3aS,6aR)-3-oxo dihydro-2H-furo[3,2-b]pyrrol-4(5H, 6H, 6aH)-yl)pentan-2-yl)benzamide;
- 4-(4-cyclopropylpiperazin-1-yl)-N—((S)-4-methyl-1-oxo-1-((3aS,6aR)-3-oxo dihydro-2H-furo[3,2-b]pyrrol-4(5H, 6H,6aH)-yl)pentan-2-yl)benzamide; and
- 4-(1-cyclobutylpiperazin-4-yl)-N—((S)-4-methyl-1-oxo-1-((3aS,6aR)-3-oxo dihydro-2H-furo[3,2-b]pyrrol-4 (5H, 6H, 6aH)-yl)pentan-2-yl)benzamide.

* * * * *